United States Patent
Nakamura et al.

(10) Patent No.: US 10,653,365 B2
(45) Date of Patent: *May 19, 2020

(54) BIOLOGICAL INFORMATION PROCESSING DEVICE AND BIOLOGICAL INFORMATION PROCESSING METHOD

(71) Applicant: PANASONIC INTELLECTUAL PROPERTY MANAGEMENT CO., LTD., Osaka (JP)

(72) Inventors: Tsuyoshi Nakamura, Fukuoka (JP); Tadanori Tezuka, Fukuoka (JP); Masatoshi Matsuo, Fukuoka (JP); Yoshinori Kumamoto, Tokyo (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 16/259,516

(22) Filed: Jan. 28, 2019

(65) Prior Publication Data

US 2019/0150853 A1 May 23, 2019

Related U.S. Application Data

(63) Continuation of application No. 15/516,791, filed as application No. PCT/JP2015/005105 on Oct. 8, 2015, now Pat. No. 10,238,345.

(30) Foreign Application Priority Data

Oct. 16, 2014 (JP) .................... 2014-211985
Oct. 16, 2014 (JP) .................... 2014-211986

(51) Int. Cl.
*A61B 5/00* (2006.01)
*A61B 5/0245* (2006.01)
(Continued)

(52) U.S. Cl.
CPC .......... *A61B 5/7275* (2013.01); *A61B 5/0077* (2013.01); *A61B 5/024* (2013.01);
(Continued)

(58) Field of Classification Search
CPC ..... A61B 5/0077; A61B 5/024; A61B 5/0245; A61B 5/117; A61B 5/7246; A61B 5/7275;
(Continued)

(56) References Cited

U.S. PATENT DOCUMENTS

2005/0187437 A1* 8/2005 Matsugu ............... A61B 5/16
600/301
2013/0096439 A1 4/2013 Lee
(Continued)

FOREIGN PATENT DOCUMENTS

EP 2438849 4/2012
EP 2772828 9/2014
(Continued)

OTHER PUBLICATIONS

Search Report issued in International Bureau of WIPO Patent Application No. PCT/JP2015/005105, dated Dec. 15, 2015.
(Continued)

*Primary Examiner* — Manuchehr Rahmjoo
(74) *Attorney, Agent, or Firm* — Greenblum & Bernstein, P.L.C.

(57) ABSTRACT

A biological information processing device and method includes selecting image ranges of processing targets from input image data, estimating pulse rates of the processing targets corresponding to the image ranges on the basis of image data of the selected image ranges of the processing targets, performing relative comparison between the estimated pulse rates of the processing targets and thus detecting a target which will possibly be abnormal or a target requiring
(Continued)

special attention, and outputting information regarding the detected target which will possibly be abnormal or the detected target requiring special attention.

15 Claims, 24 Drawing Sheets

(51) Int. Cl.

| | | |
|---|---|---|
| A61B 5/117 | (2016.01) | |
| G16H 30/20 | (2018.01) | |
| G16H 30/40 | (2018.01) | |
| G16H 50/20 | (2018.01) | |
| G06T 7/11 | (2017.01) | |
| A61B 5/024 | (2006.01) | |
| G06K 9/46 | (2006.01) | |
| G06K 9/62 | (2006.01) | |
| G06T 7/00 | (2017.01) | |
| G16H 50/30 | (2018.01) | |

(52) U.S. Cl.
CPC .......... *A61B 5/0245* (2013.01); *A61B 5/117* (2013.01); *A61B 5/7246* (2013.01); *G06K 9/4604* (2013.01); *G06K 9/6202* (2013.01); *G06T 7/0012* (2013.01); *G06T 7/11* (2017.01); *G16H 30/20* (2018.01); *G16H 30/40* (2018.01); *G16H 50/20* (2018.01); *G16H 50/30* (2018.01)

(58) Field of Classification Search
CPC .. G06K 9/4604; G06K 9/6202; G06T 7/0012; G06T 7/11; G16H 30/20; G16H 30/40; G16H 50/20; G16H 50/30
See application file for complete search history.

(56) References Cited

U.S. PATENT DOCUMENTS

| | | | |
|---|---|---|---|
| 2013/0215928 A1* | 8/2013 | Bellifemine | G01J 5/0022 374/121 |
| 2014/0254902 A1 | 9/2014 | Sugawara et al. | |
| 2016/0338603 A1* | 11/2016 | Nakata | A61B 5/02416 |
| 2017/0325686 A9 | 11/2017 | Shan | |

FOREIGN PATENT DOCUMENTS

| | | |
|---|---|---|
| JP | 05-184578 | 7/1993 |
| JP | 2010-051592 | 3/2010 |
| JP | 2011-236020 A | 11/2011 |
| JP | 2013-090847 A | 5/2013 |
| JP | 2014-036801 | 2/2014 |
| WO | 2013/027141 | 2/2013 |
| WO | 2014/147496 A1 | 9/2014 |

OTHER PUBLICATIONS

Extended European Search Report dated Sep. 21, 2017 for the related European Patent Application No. 15850716.0.
Ming-Zher Poh et al: "Non-contact, automated cardiac pulse measurements using video imaging and blind source separation", Optics Express, vol. 18, No. 10, May 10, 2010 (May 10, 2010), p. 10762, XP055016649.

\* cited by examiner

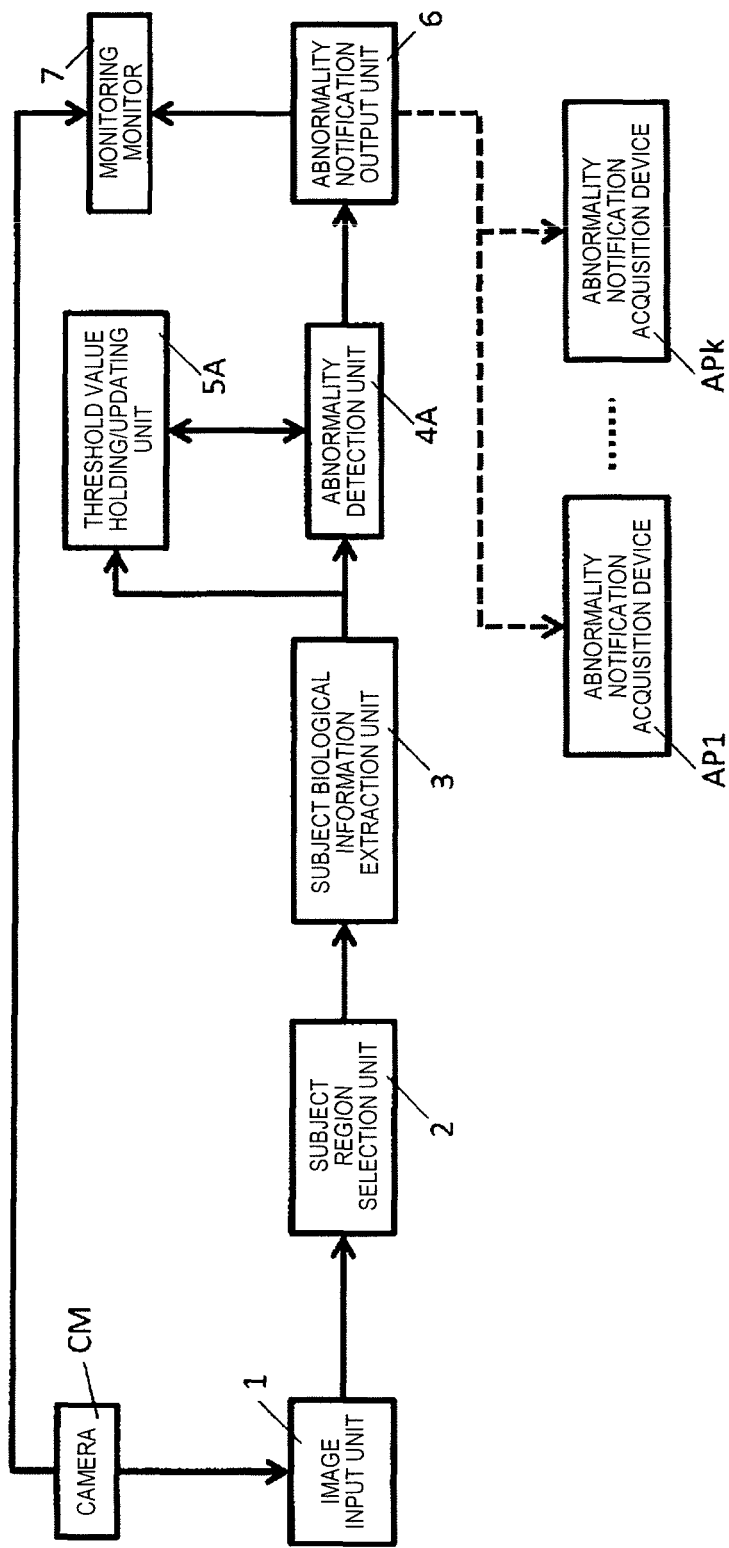

BIOLOGICAL INFORMATION PROCESSING DEVICE AND BIOLOGICAL INFORMATION PROCESSING METHOD

CROSS REFERENCE TO RELATED APPLICATION

This is a continuation application of U.S. patent application Ser. No. 15/516,791, filed Apr. 4, 2017, which is a National Phase application of International Application No. PCT/JP2015/005105, filed on Oct. 8, 2015, and which claims the benefit of Japanese Patent Application No. 2014-211985, filed Oct. 16, 2014, and Japanese Application No. 2014-211986, filed Oct. 16, 2014, the disclosures of which are expressly incorporated herein by reference in their entireties.

TECHNICAL FIELD

The present invention relates to a biological information processing device and a biological information processing method capable of monitoring biological information of a person.

BACKGROUND ART

A vital sensing technique of estimating biological information of a person is expected to be applied not only to, for example, a home medical field or a health management field, but also to various fields such as detection of drowsiness during driving, acquisition of a mental state of a user during gaming, and detection of an abnormal person in a monitoring system. At present, most types of apparatuses sensing biological information are used to come into contact with a person's body, and a user is required to attach an apparatus thereto. Therefore, an application range thereof is restricted.

Thus, as one of countermeasures for sensing in a non-contact manner, there has been proposed a technique of estimating a pulse rate as an example of biological information on the basis of an image obtained through imaging in a camera. By using this technique, biological information can be sensed without a user's awareness, and thus it can be expected to enlarge an application range. For example, it is possible to detect a suspicious person whose pulse change increases due to stress while imaging with a monitoring camera. The technique also has a great advantage in that a plurality of people imaged by a single camera can be sensed together. When compared with a contact type, an individual apparatus is not required to be provided for each user, and it is also possible to reduce troublesomeness of attaching an apparatus to a body.

Here, regarding the related art of observing (monitoring) a biological state of a person, for example, there is a biological state observation system disclosed in PTL 1. In the biological state observation system, an image including at least one person to be observed, formed of a plurality of time-variant continuous frames, is input; a predetermined region in the image is detected, and information regarding the detected predetermined region is output; the biological information of the person to be observed included in the image is detected from the predetermined region in the image; and a predetermined biological parameter used for determining the abnormality of the biological state is compared with biological information data or a change in the biological information data so that the abnormality occurring in the biological state of the person to be observed is detected. Consequently, the biological state observation system can observe biological information of the person to be observed and detect the abnormality of the biological state of the person to be observed without giving discomfort and unpleasantness to the person to be observed. In PTL 1, the biological parameter used for comparison has a predetermined fixed value or a value which is updated via the Internet, and, when biological information of a person to be observed is observed, an abnormal person to be observed (a subject or a biological information processing target) is determined by using the value of the biological parameter.

As the related art regarding a pulse estimation technique using a camera, for example, there is a pulse measurement device disclosed in PTL 2. The pulse measurement device calculates a feature amount of a captured input image, detects a peak interval of a pulse wave on the basis of the calculated feature amount, and calculates a pulse rate on the basis of the detected peak interval of the pulse wave. The pulse measurement device controls a frame rate indicating the number of frames captured per unit time so that an estimated maximum error between a pulse rate having a valid peak interval based on an adoption proportion indicating a proportion of the valid peak interval in the calculated pulse rate and a true pulse rate is equal to or less than a prescribed value.

CITATION LIST

Patent Literature

PTL 1: Japanese Patent Unexamined Publication No. 2014-36801
PTL 2: Japanese Patent Unexamined Publication No. 2010-51592

SUMMARY OF THE INVENTION

An object of the present disclosure is to detect accurately and in real time a pulse rate of a subject who will possibly be abnormal or a subject as a target requiring special attention among a plurality of subjects (processing targets) by tracking a change in a surrounding environment even in a case where the change in the surrounding environment occurs.

According to the present disclosure, there is provided a biological information processing device including an image input unit that inputs image data, a selection unit, an estimation unit, a detection unit, and an output unit. The selection unit selects image ranges of processing targets from the image data which is input by the image input unit. The estimation unit estimates pulse rates of the processing targets corresponding to the image ranges on the basis of image data of the selected image ranges of the processing targets. The detection unit performs relative comparison between the estimated pulse rates of the processing targets and thus detects a target which will possibly be abnormal or a target requiring special attention. The output unit outputs information regarding the detected target which will possibly be abnormal or the detected target requiring special attention.

According to the present disclosure, there is provided a biological information processing method in the biological information processing device. The method includes the following steps: a step of inputting image data; a step of selecting image ranges of processing targets from the input image data; a step of estimating pulse rates of the processing targets corresponding to the same image ranges on the basis of image data of the selected image ranges of the processing targets; a step of performing relative comparison between the estimated pulse rates of the processing targets and thus detecting a target which will possibly be abnormal or a target requiring special attention; and a step of outputting information regarding the detected target which will possibly be abnormal or the detected target requiring special attention.

According to the present disclosure, it is possible to detect accurately and in real time a pulse rate of a subject who will possibly be abnormal or a subject as a target requiring special attention among a plurality of subjects by tracking a change in a surrounding environment even in a case where the change in the surrounding environment occurs.

BRIEF DESCRIPTION OF DRAWINGS

FIG. 7 is a block diagram illustrating an example of an internal configuration of a biological information processing device according to a second exemplary embodiment.

DESCRIPTION OF EMBODIMENTS

Figure 1A:
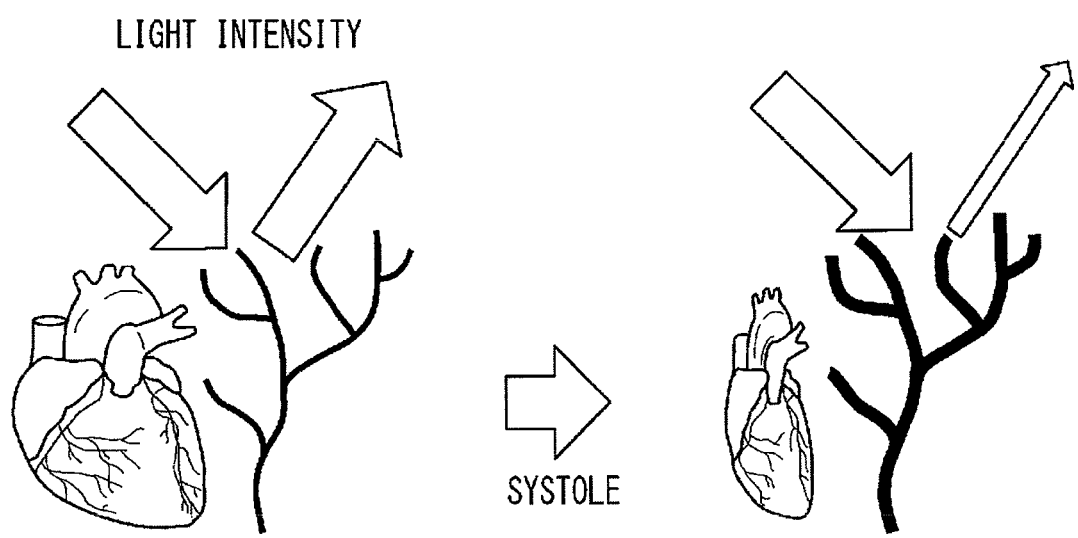
FIG. 1A is a schematically illustrating an example of a relationship between contraction of the heart of a person and a light absorption amount of a blood vessel.
Figure 1B:
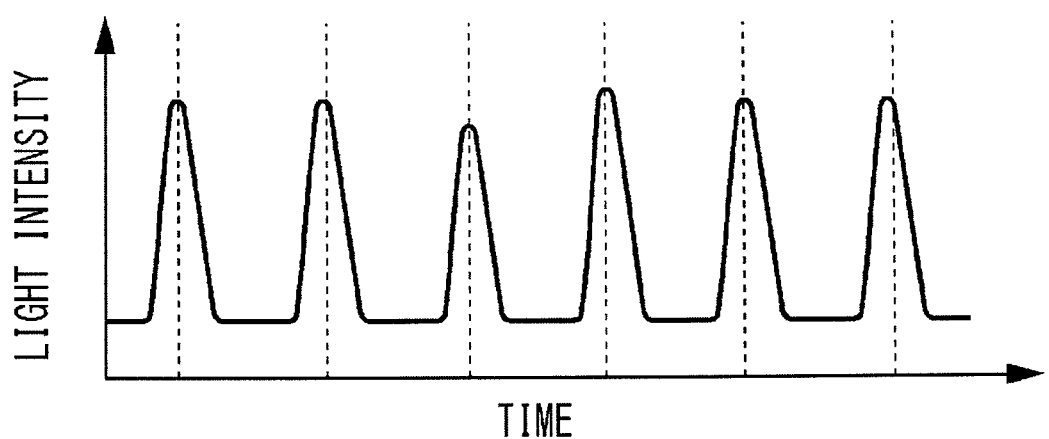
FIG. 1B is a diagram illustrating an example of a time-series change of light intensity.

First, with reference to FIGS. 1A and 1B, a description will be made of a pulse rate estimation principle in a biological information processing device according to each exemplary embodiment. FIG. 1A is a schematically illustrating an example of a relationship between contraction of the heart of a person and a light absorption amount of a blood vessel. FIG. 1B is a diagram illustrating an example of a time-series change of light intensity.

FIG. 1A illustrates that a volume of a blood vessel changes in synchronization with contraction (systole) of the heart of a person. If the volume of the blood vessel increases due to the contraction of the heart, an amount of absorbed light (for example, light in a specific wavelength range illustrated in FIG. 2) increases, and thus light intensity is reduced (refer to FIG. 1B). In the following description, a pulse wave indicates movement of a wave when a pressure change in a blood vessel occurring at the time of blood being pushed to the main artery due to contraction of the heart is transferred in a peripheral direction.

In FIG. 1B, a transverse axis expresses time, and a longitudinal axis expresses the intensity of a signal (photoelectric pulse wave) obtained due to a change in a light absorption amount. In other words, in FIG. 1B, since a light absorption amount is small when a peak appears, a state occurs in which a volume of a blood vessel does not increase. Since a light absorption amount is large when the minimum value appears, a state occurs in which the volume of the blood vessel increases. The contraction of the heart and a change in the intensity of the photoelectric pulse wave fundamentally fluctuate in synchronization with each other although complete synchronization does not occur due to a distance between the heart and a peripheral part and thus there is slight delay.

Figure 2:
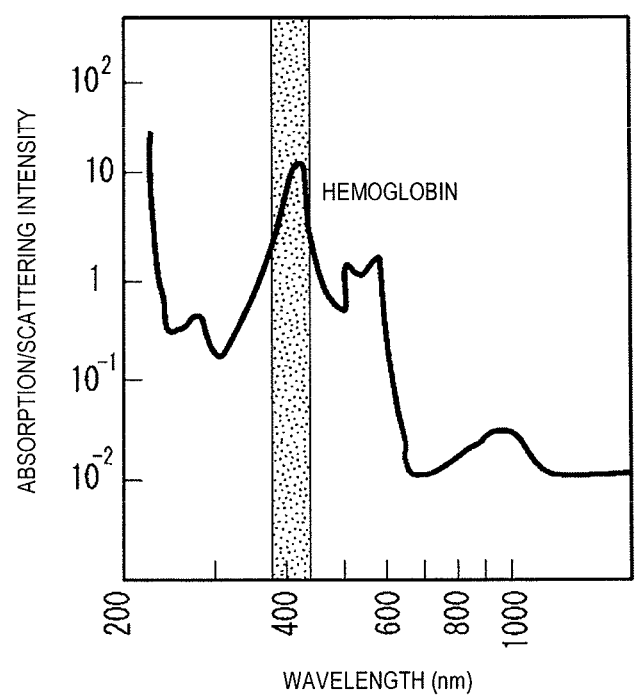
FIG. 2 is a diagram illustrating an example of an absorption rate for each wavelength of light in hemoglobin.

FIG. 2 is a diagram illustrating an example of an absorption rate for each wavelength of light in hemoglobin. FIG. 2 illustrates that, for example, hemoglobin (blood) tends to absorb a wavelength of 400 nm (that is, green). In the following respective exemplary embodiments, the embodiments will be described by using the fact that an absorption rate of a green light component is high, but, for example, a reflection rate of a red light (having a wavelength of over 1000 nm, for example) component is high.

First Exemplary Embodiment

Figure 3:
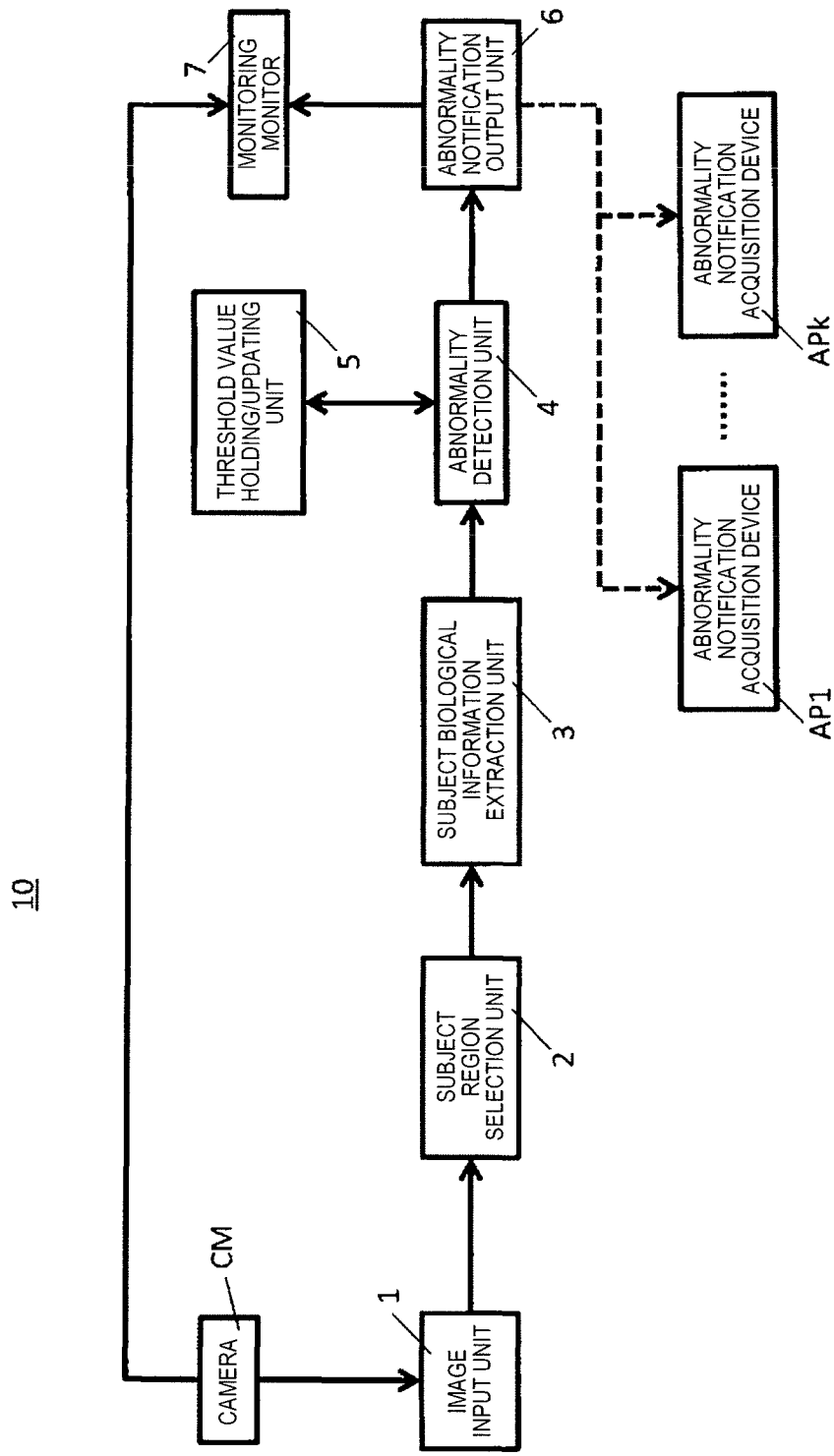
FIG. 3 is a block diagram illustrating an example of an internal configuration of a biological information processing device according to a first exemplary embodiment.

Hereinafter, with reference to FIG. 3, a description will be made of a configuration of a biological information processing device according to a first exemplary embodiment. FIG. 3 is a block diagram illustrating an example of an internal configuration of biological information processing device 10 according to the first exemplary embodiment. Biological information processing device 10 illustrated in FIG. 3 is configured to include camera CM, image input unit 1, subject region selection unit 2 (region selection unit), subject biological information extraction unit 3 (extraction unit), abnormality detection unit 4, threshold value holding/updating unit 5, abnormality notification output unit 6, and monitoring monitor 7. Biological information processing device 10 may be configured to further include abnormality notification acquisition devices AP1, . . . , and APk (which will be described later).

Camera CM captures an image of n subjects as estimation target objects at a predetermined frame rate (for example, 10 frames per second (fps)), and outputs the image to image input unit 1. Camera CM may not be included in biological information processing device 10, and may be connected to biological information processing device 10 via, for example, a network. The network is the Internet or an intranet with a wireless network or a wired network as an interface. The wireless network is, for example, a wireless local area network (LAN), a wireless wide area network (WAN), 3G, Long Term Evolution (LTE), or Wireless Gigabit (WiGig). The wired network is, for example, IEEE 802.3 or ETHERNET (registered trademark).

Image input unit 1 continuously receives (acquires), from camera CM, frames of image data obtained by camera CM imaging a person at a predetermined frame rate, and outputs the frames of image data to subject region selection unit 2. In a case where camera CM is provided separately from biological information processing device 10, image input unit 1 continuously receives frames of image data transmitted from camera CM.

Subject region selection unit 2 as an example of a selection unit selects and cuts out designated ranges RN1, RN2 and RN3 (refer to FIG. 4B) which are image ranges including respective subjects among a plurality of subjects (for example, three persons such as A, B, and C; this is also the same for the following description) in each frame (refer to FIG. 4A) of the image data which is input from image input unit 1, and outputs image data of designated range RN1 of A, designated range RN2 of B, and designated range RN3 of C to subject biological information extraction unit 3.

Figure 4A:
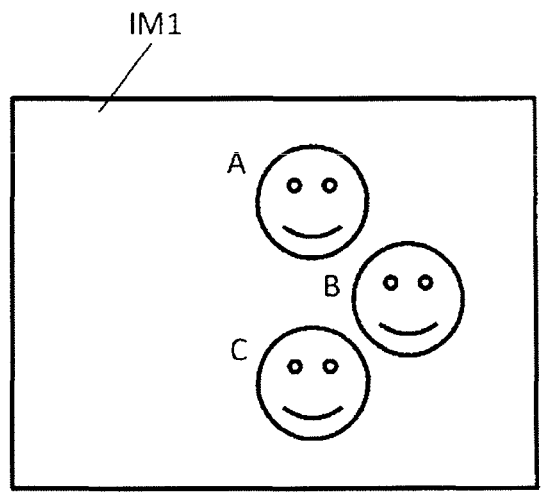
FIG. 4A is a diagram illustrating an example of a captured image of a plurality of subjects, input from a camera.
Figure 4B:
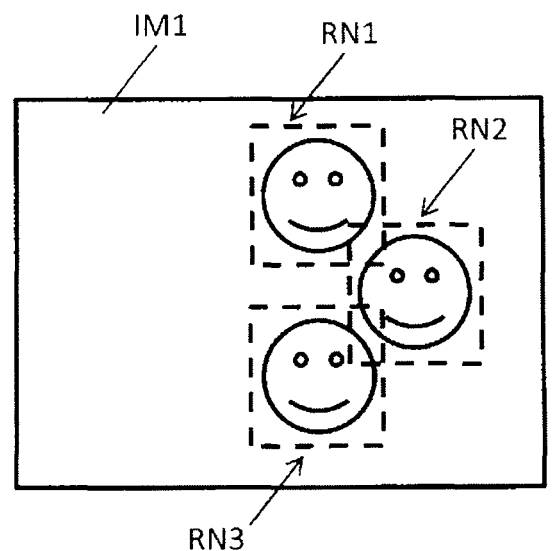
FIG. 4B is a diagram illustrating examples of a designated range of each subject which is cut out by a subject region selection unit.

FIG. 4A is a diagram illustrating an example of captured image IM1 of a plurality of subjects, input from camera CM. FIG. 4B is a diagram illustrating examples of a designated range of each subject which is cut out by subject region selection unit 2. For example, in a case where three persons such as A, B, and C are imaged by camera CM as a plurality of subjects, subject region selection unit 2 performs, for example, a well-known face detection process on data of captured image IM1, so as to detect designated range RN1 of A, designated range RN2 of B, and designated range RN3 of C, respectively, and selects and cuts out the detection results (image data of designated range RN1 of A, designated range RN2 of B, and designated range RN3 of C).

Subject biological information extraction unit 3 as an example of an estimation unit estimates pulse rates as an example of biological information of the subjects (A, B, and C) respectively corresponding to designated ranges RN1, RN2 and RN3 on the basis of the image data of designated ranges RN1, RN2 and RN3 which are image ranges including the respective subjects, output from subject region selection unit 2. Subject biological information extraction unit 3 outputs information regarding pulse rates of A, B, and C as estimation results to abnormality detection unit 4. A method of estimating a pulse rate in subject biological information extraction unit 3 is a well-known technique, and thus a detailed description thereof will be omitted.

As an example of a method of estimating a pulse rate, subject biological information extraction unit 3 extracts time (pulse wave interval: PWI) corresponding to one cycle on the basis of a signal of at least one cycle regarding pixel values of a skin color portion in a plurality of frames of the image data of A corresponding to designated range RN1 cut out by subject region selection unit 2, and calculates a pulse rate of A by using the extracted PWI and Equation (1). Similarly, subject biological information extraction unit 3 extracts time (pulse wave interval: PWI) corresponding to one cycle on the basis of a signal of at least one cycle regarding pixel values of a skin color portion in a plurality of frames of the image data of B and C corresponding to designated ranges RN2 and RN3 cut out by subject region selection unit 2, and calculates pulse rates of B and C by using the extracted PWI and Equation (1).

$$\text{Pulse Rate} = 60/\text{PWI} \tag{1}$$

Abnormality detection unit 4 as an example of a detection unit relatively compares (for example, retrieves the maximum value) the pulse rate calculation results (estimation results) of the plurality of subjects (A, B, and C) output from subject biological information extraction unit 3 with each other, so as to detect a subject who will possibly be abnormal or a subject as a target requiring special attention, and outputs a detection result to abnormality notification output unit 6. Abnormality detection unit 4 stores a threshold value obtained through relative comparison in threshold value holding/updating unit 5. The threshold value mentioned in the present exemplary embodiment is a determination value (maximum value) of a pulse rate used for specifying a subject who will possibly be abnormal or a subject as a target requiring special attention among a plurality of subjects (for example, A, B, and C) who are pulse rate estimation targets. Therefore, in the present exemplary embodiment, a subject whose pulse rate is less than the threshold value is not detected as a subject who will possibly be abnormal or a subject as a target requiring special attention.

First, abnormality detection unit 4 stores the pulse rate of A among the pulse rate calculation results (estimation results) of the plurality of subjects (A, B, and C) output from subject biological information extraction unit 3, in threshold value holding/updating unit 5 as an individual variation of the threshold value, and then compares the pulse rate calculation results with each other in order.

Specifically, abnormality detection unit 4 relatively compares the pulse rate of A with the pulse rate of B, selects the pulse rate of B as a threshold value in a case where the pulse rate of B is higher than the pulse rate of A (refer to FIG. 4C), and updates the threshold value in threshold value holding/updating unit 5 to the pulse rate of B. Next, abnormality detection unit 4 relatively compares the pulse rate of B with the pulse rate of C, selects the pulse rate of C as a threshold value in a case where the pulse rate of C is higher than the pulse rate of B (refer to FIG. 4C), and updates the threshold value in threshold value holding/updating unit 5 to the pulse rate of C.

Figure 4C:
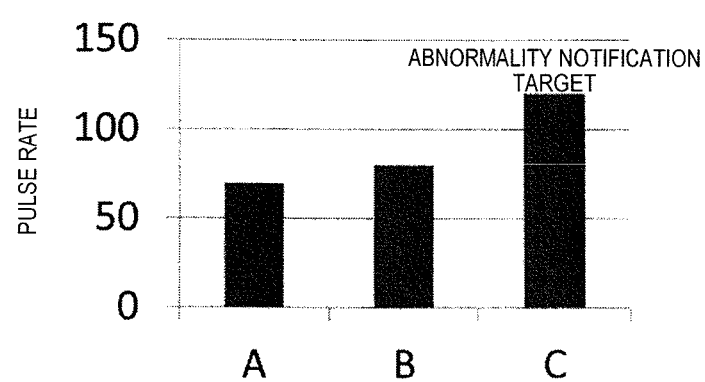
FIG. 4C is a diagram illustrating an example of an extraction result of a pulse rate of each subject.

Abnormality detection unit 4 relatively compares the pulse rate of C with the pulse rate of A, selects the pulse rate of A as a threshold value in a case where the pulse rate of A is higher than the pulse rate of C, and updates the threshold value in threshold value holding/updating unit 5 to the pulse rate of A, but holds the pulse rate of C in threshold value holding/updating unit 5 as a threshold value in a case where the pulse rate of C is higher than the pulse rate of A (refer to FIG. 4C). FIG. 4C is a diagram illustrating an example of an extraction result of a pulse rate of each subject. In the example illustrated in FIG. 4C, the pulse rate of C is higher than the pulse rates of the two other persons (A and B), and thus abnormality detection unit 4 detects C corresponding to the pulse rate selected as the threshold value, as a subject who will possibly be abnormal or a subject as a target requiring special attention.

Threshold value holding/updating unit 5 is formed by using, for example, a random access memory (RAM), a semiconductor memory, a hard disk drive (HDD), or a solid state drive (SSD), and stores a value indicating a pulse rate selected and held or a pulse rate updated by abnormality detection unit 4.

Abnormality notification output unit 6 outputs information regarding the subject who will possibly be abnormal or the subject as a target requiring special attention to monitoring monitor 7 on the basis of a detection result output from abnormality detection unit 4.

Figure 5:
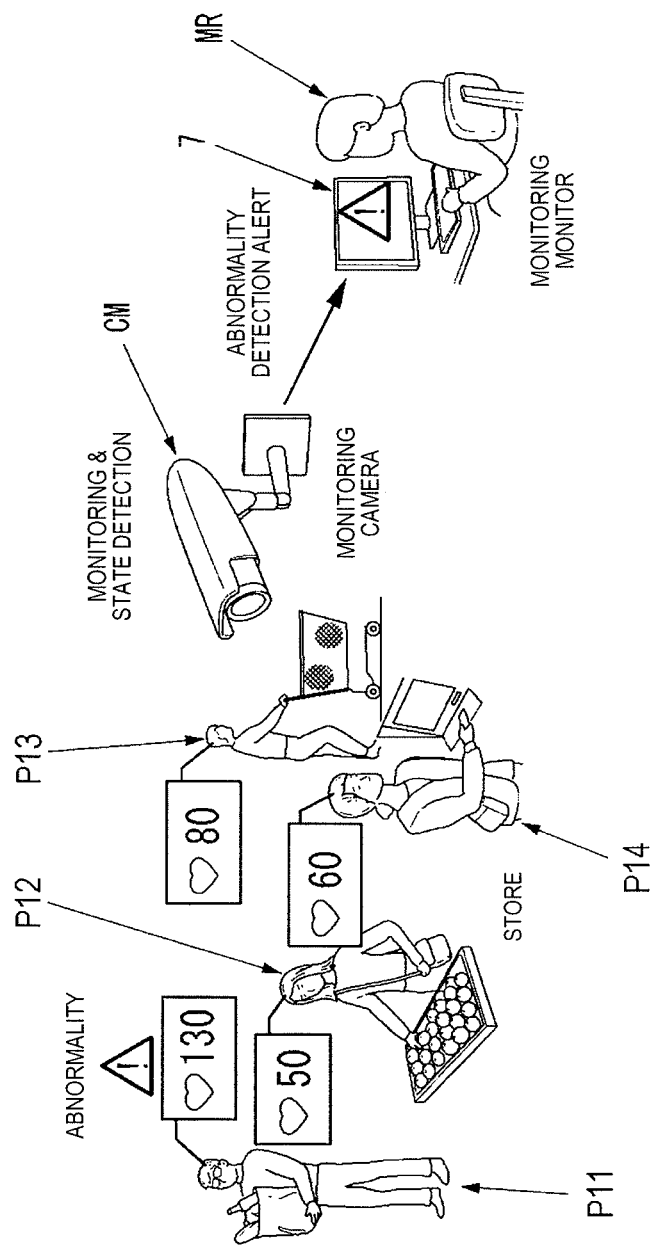
FIG. 5 is a diagram illustrating an example in which a biological information processing device according to each exemplary embodiment is used.

Regarding an output aspect, abnormality notification output unit 6 displays the information regarding the subject who will possibly be abnormal or the subject as a target requiring special attention on monitoring monitor 7 in an identifiable manner, for example, in a case where biological information processing device 10 includes monitoring monitor 7 (refer to FIG. 5). FIG. 5 is a diagram illustrating an example in which biological information processing device 10 according to each exemplary embodiment or biological information processing device 10A illustrated in FIG. 7 is used. As an identifiable display example, abnormality notification output unit 6 displays a marker (for example, an exclamation mark) indicating a subject who will possibly be abnormal or a subject as a target requiring special attention around corresponding subject P1 on monitoring monitor 7.

In FIG. 5, for example, in a case where biological information processing device 10 of the present exemplary embodiment is provided in a store, subjects (shoppers) in the store are imaged by a monitoring camera (camera CM). Pulse rates of four subjects P11, P12, P13 and P14 are estimated in a noncontact manner. Pulse rates as estimation results and a marker indicating that there is a subject who will possibly be abnormal or a subject as a target requiring special attention are displayed on monitoring monitor 7 provided in a monitoring room (for example, a back office of the store). Consequently, person MR in charge of the store (for example, a manager of the store) can recognize that there is a subject (shopper) who will possibly be abnormal or a subject (shopper) as a target requiring special attention.

Regarding another output aspect, for example, in a case where biological information processing device 10 includes a speaker (not illustrated), abnormality notification output unit 6 may output sounds for information regarding a subject who will possibly be abnormal or a subject as a target requiring special attention from the speaker. Consequently, person MR in charge of the store (for example, a manager of the store) can simply recognize that there is a subject (shopper) who will possibly be abnormal or a subject (shopper) as a target requiring special attention with only sounds from the speaker without viewing monitoring monitor 7.

Monitoring monitor 7 is a display formed by using, for example, a liquid crystal display (LCD) or organic electroluminescence, displays image data captured by camera CM, and further displays a marker indicating a subject who will possibly be abnormal or a subject as a target requiring special attention around the corresponding subject on the basis of information regarding the corresponding subject output from abnormality notification output unit 6 as necessary. For example, in a case where biological information processing device 10 is provided in a store, monitoring monitor 7 is preferably provided in the monitoring room (a back office of the store).

Abnormality notification acquisition devices AP1, . . . , and APk (where k is an integer of 1 or more) are provided output destinations of information regarding a subject who will possibly be abnormal or a subject as a target requiring special attention from abnormality notification output unit 6 other than monitoring monitor 7, and support, for example, monitoring work of a person in charge of the store (for example, a manager of the store) present in the monitoring room on monitoring monitor 7. Abnormality notification acquisition devices AP1, . . . , and APk is any one or a combination of, for example, a wrist band having a wireless communication function using Bluetooth (registered trademark) and a vibration function, a head mounted display having a wireless communication function, and, for example, an illumination device or a sound output device provided in the store.

For example, in a case where abnormality notification acquisition devices AP1, . . . , and APk are wrists bands having a wireless communication function and a vibration function, and respective salespersons in the store mount abnormality notification acquisition devices AP1, . . . , and APk (where k is an integer of 1 or more) thereon, respective abnormality notification acquisition devices AP1, . . . , and APk cause the vicinity function to work according to an output from abnormality notification output unit 6, and can thus notify the salespersons that there is a subject who will possibly be abnormal or a subject as a target requiring special attention. Consequently, for example, a salesperson closest to the monitoring room can protect the corresponding subject or can monitor whether or not the subject performs a suspicious behavior by referring to a marker displayed on monitoring monitor 7.

For example, in a case where abnormality notification acquisition devices AP1, . . . , and APk are head mounted displays having a wireless communication function, and, similarly, respective salespersons in the store mount abnormality notification acquisition devices AP1, . . . , and APk (where k is an integer of 1 or more) thereon, respective abnormality notification acquisition devices AP1, . . . , and APk can notify the salespersons that there is a subject who will possibly be abnormal or a subject as a target requiring special attention on the head mounted displays according to an output from abnormality notification output unit 6. Consequently, for example, a salesperson closest to the corresponding subject can protect the corresponding subject or can monitor whether or not the subject performs a suspicious behavior without checking a marker displayed on monitoring monitor 7.

For example, in a case where abnormality notification acquisition devices AP1, . . . , and APk are illumination devices (for example, light emitting diodes (LEDs)) or sound output devices (for example, speakers) provided in the store, respective abnormality notification acquisition devices AP1, . . . , and APk can notify the salespersons that there is a subject who will possibly be abnormal or a subject as a target requiring special attention through an illumination pattern or a sound change which is hardly noticed by people (for example, shoppers) other than the store manager or the salespersons according to an output from abnormality notification output unit 6. Consequently, for example, a salesperson closest to the corresponding subject can protect the corresponding subject or can monitor whether or not the subject performs a suspicious behavior at a target position in the store corresponding to the illumination pattern or the sound without checking a marker displayed on monitoring monitor 7.

Figure 6:
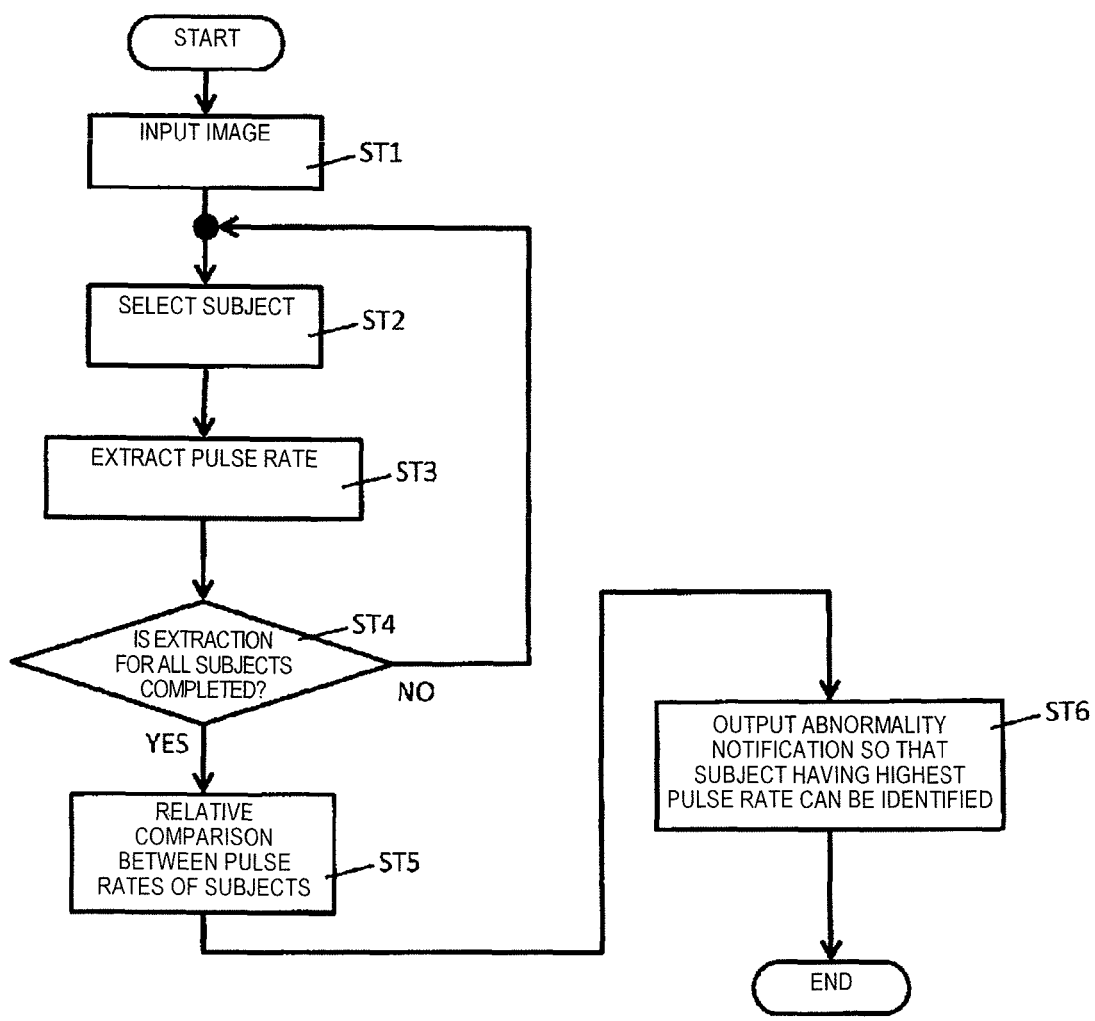
FIG. 6 is a flowchart illustrating examples of operation procedures in the biological information processing device according to the first exemplary embodiment.

Next, with reference to FIG. 6, a description will be made of examples of operation procedures in biological information processing device 10 of the present exemplary embodiment. FIG. 6 is a flowchart illustrating examples of operation procedures in biological information processing device 10 according to the first exemplary embodiment.

In FIG. 6, image input unit 1 continuously receives (acquires), from camera CM, frames of image data obtained by camera CM imaging a person at a predetermined frame rate, and outputs the frames of image data to subject region selection unit 2 (ST1). Subject region selection unit 2 selects and cuts out designated ranges RN1, RN2 and RN3 (refer to FIG. 4B) which are image ranges including respective subjects among a plurality of subjects (A, B, and C) in each frame (refer to FIG. 4A) of the image data which is input from image input unit 1 (ST2). Subject region selection unit 2 outputs image data of designated range RN1 of A, designated range RN2 of B, and designated range RN3 of C to subject biological information extraction unit 3.

Subject biological information extraction unit 3 estimates pulse rates as an example of biological information of the subjects (A, B, and C) respectively corresponding to designated ranges RN1, RN2 and RN3 on the basis of the image data of designated ranges RN1, RN2 and RN3 which are image ranges including the respective subjects, output from subject region selection unit 2 (ST3). Subject biological information extraction unit 3 outputs information regarding pulse rates of A, B, and C as estimation results to abnormality detection unit 4. The processes in step ST2 and step ST3 are repeatedly performed until subject biological information extraction unit 3 calculates pulse rates of all the subjects (A, B, and C) (ST4, NO).

On the other hand, in a case where subject biological information extraction unit 3 calculates pulse rates of all the subjects (A, B, and C) (ST4, YES), abnormality detection unit 4 relatively compares (for example, retrieves the maximum value) the pulse rate calculation results (estimation results) of the plurality of subjects (A, B, and C) output from subject biological information extraction unit 3 with each other (ST5), so as to detect a subject who will possibly be abnormal or a subject as a target requiring special attention, and outputs a detection result to abnormality notification output unit 6. Abnormality detection unit 4 stores a threshold value obtained through relative comparison in threshold value holding/updating unit 5.

Abnormality notification output unit 6 outputs, for example, information regarding a subject whose pulse rate is highest among all of the subjects, to monitoring monitor 7 as information regarding a subject who will possibly be abnormal or a subject as a target requiring special attention, on the basis of a detection result output from abnormality detection unit 4 (ST6). Abnormality notification output unit 6 displays a marker (for example, an exclamation mark) indicating a subject who will possibly be abnormal or a subject as a target requiring special attention around corresponding subject P1 on monitoring monitor 7.

As mentioned above, biological information processing device 10 of the present exemplary embodiment selects designated ranges RN1, RN2 and RN3 which are image ranges of respective subjects from image data obtained by imaging n subjects (for example, A, B, and C), and estimates pulse rates of subjects corresponding to the image ranges on the basis of image data of selected designated ranges RN1, RN2 and RN3 which are the image ranges of the respective subjects. Biological information processing device 10 detects a subject who will possibly be abnormal or a subject as a target requiring special attention according to relative comparison between the estimated pulse rates of all of n subjects, and outputs information regarding a subject corresponding to a detection result.

In a case where a surrounding environment changes (for example, a room temperature or an atmospheric temperature changes) when biological information (for example, a pulse rate) of a subject is estimated, a pulse rate also increases according to an increase in the room temperature or the atmospheric temperature. Biological information processing device 10 performs relative comparison between pulse rate estimation results for all subjects through the above-described processes, and thus detects a subject whose value of a pulse rate is higher (conspicuous) than other subjects. Thus, biological information processing device 10 can detect accurately and in real time a pulse rate of a subject who will possibly be abnormal or a subject as a target requiring special attention among a plurality of subjects (processing targets) by tracking a change in a surrounding environment, compared with a technique using a constant threshold value in order to estimate a pulse rate.

Since biological information processing device 10 compares estimated pulse rates of n subjects in order, and detects a subject corresponding to the highest pulse rate as a subject who will possibly be abnormal or a subject as a target requiring special attention, a subject whose pulse rate is higher than those of other subjects and thus who is conspicuous as a result of the relative comparison can be detected as a subject who will possibly be abnormal or a subject as a target requiring special attention.

Since biological information processing device 10 can update and hold the highest pulse rate among estimated pulse rates of n subjects as a threshold value, it is possible to detect a subject having a pulse rate of the subject who will possibly be abnormal or the subject as a target requiring special attention by using a threshold value as the maximum value updated in the previous estimation and by tracking a change in a surrounding environment, for example, when pulse rates of a plurality of subjects are periodically estimated, compared with a technique using a constant threshold value.

Second Exemplary Embodiment

FIG. 7 is a block diagram illustrating an example of an internal configuration of biological information processing device 10A according to a second exemplary embodiment. In biological information processing device 10A illustrated in FIG. 7, units having the same configurations as the respective units of biological information processing device 10 illustrated in FIG. 3 are given the same reference numerals so that description thereof will be made briefly or omitted, and differing content will be described.

Biological information processing device 10A illustrated in FIG. 7 is configured to include camera CM, image input unit 1, subject region selection unit 2, subject biological information extraction unit 3, abnormality detection unit 4A, threshold value holding/updating unit 5A, abnormality notification output unit 6, and monitoring monitor 7. In the same manner as in the first exemplary embodiment, biological information processing device 10A may be configured to further include abnormality notification acquisition devices AP1, . . . , and APk (which will be described later). In description of the present exemplary embodiment, configurations of abnormality notification acquisition devices AP1, . . . , and APk are the same as those in the first exemplary embodiment, and thus description thereof will be omitted.

Abnormality detection unit 4A as an example of a detection unit relatively compares (for example, calculates an average value) the pulse rate calculation results (estimation results) of the plurality of subjects (A, B, and C) output from subject biological information extraction unit 3 with each other, so as to detect a subject who will possibly be abnormal or a subject as a target requiring special attention, and outputs a detection result to abnormality notification output unit 6. Abnormality detection unit 4A stores a threshold value (average value) obtained through relative comparison in threshold value holding/updating unit 5A. The threshold value mentioned in the present exemplary embodiment is a determination value (average value) of a pulse rate used for specifying a subject who will possibly be abnormal or a subject as a target requiring special attention among a plurality of subjects (for example, A, B, and C) who are pulse rate estimation targets. Therefore, in the present exemplary embodiment, a subject whose pulse rate is less than the threshold value is not detected as a subject who will possibly be abnormal or a subject as a target requiring special attention.

First, abnormality detection unit 4A calculates an average value of the pulse rate calculation results (estimation results) of the plurality of subjects (A, B, and C) output from subject biological information extraction unit 3, and updates an initial value of a threshold value stored in threshold value holding/updating unit 5A in advance to the calculated average value.

Figure 8A:
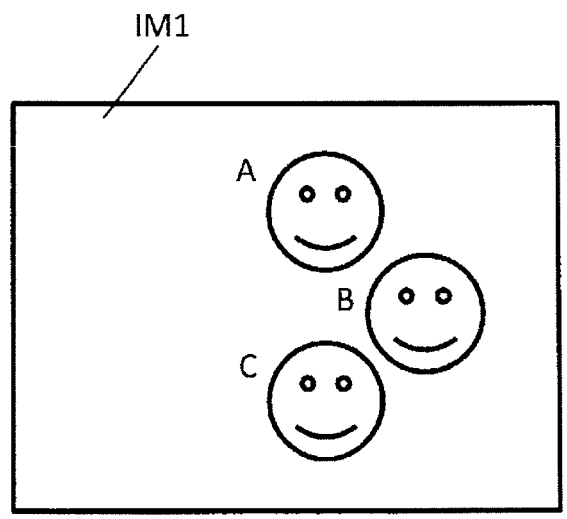
FIG. 8A is a diagram illustrating an example of a captured image of a plurality of subjects, input from a camera.
Figure 8B:
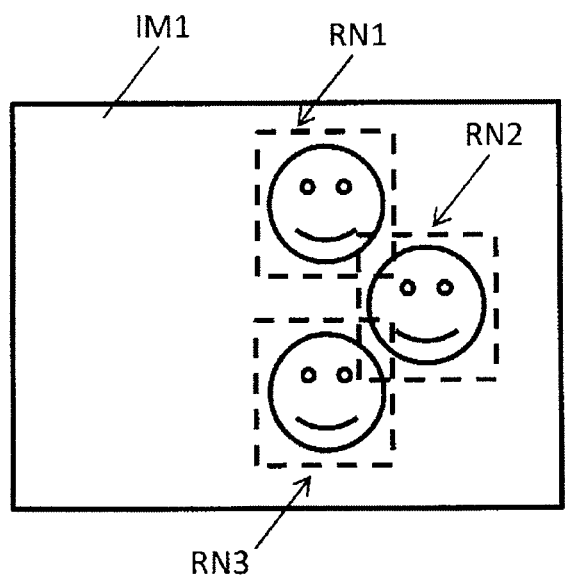
FIG. 8B is a diagram illustrating examples of a designated range of each subject which is cut out by a subject region selection unit.
Figure 8C:
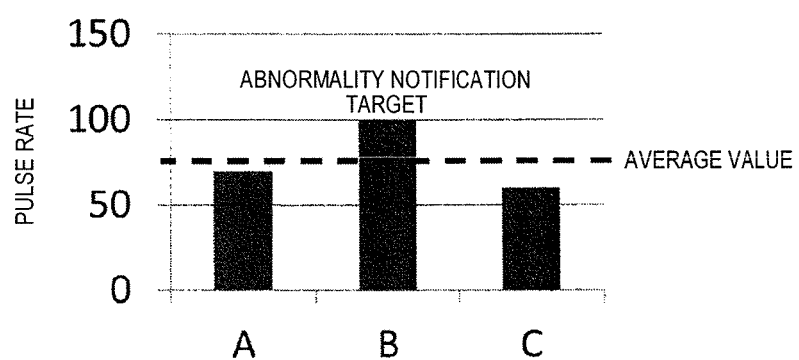
FIG. 8C is a diagram illustrating an example of an extraction result of a pulse rate of each subject.

Abnormality detection unit 4A relatively compares the pulse rates of A, B, and C with the threshold value (average value). Since the pulse rate of A and the pulse rate of C are less than the average value (refer to FIG. 8C), A and C are excluded as a subject who will possibly be abnormal or a subject as a target requiring special attention. Abnormality detection unit 4A detects B whose pulse rate is more than the average value illustrated in FIG. 8C as a subject who will possibly be abnormal or a subject as a target requiring special attention. FIG. 8C is a diagram illustrating an example of an extraction result of a pulse rate of each subject. In the example illustrated in FIG. 8C, since the pulse rate of B is higher than the pulse rates of the two other persons (A and C) and exceeds the threshold value, abnormality detection unit 4A detects B whose pulse rate exceeds the threshold value as a subject who will possibly be abnormal or a subject as a target requiring special attention. FIGS. 8A and 8B are the same as FIGS. 4A and 4B, and thus description thereof will be omitted.

Threshold value holding/updating unit 5A is formed by using, for example, a RAM, a semiconductor memory, an HDD, or an SSD, and stores an average value of pulse rates of respective subjects calculated by abnormality detection unit 4A as a threshold value.

Figure 9:
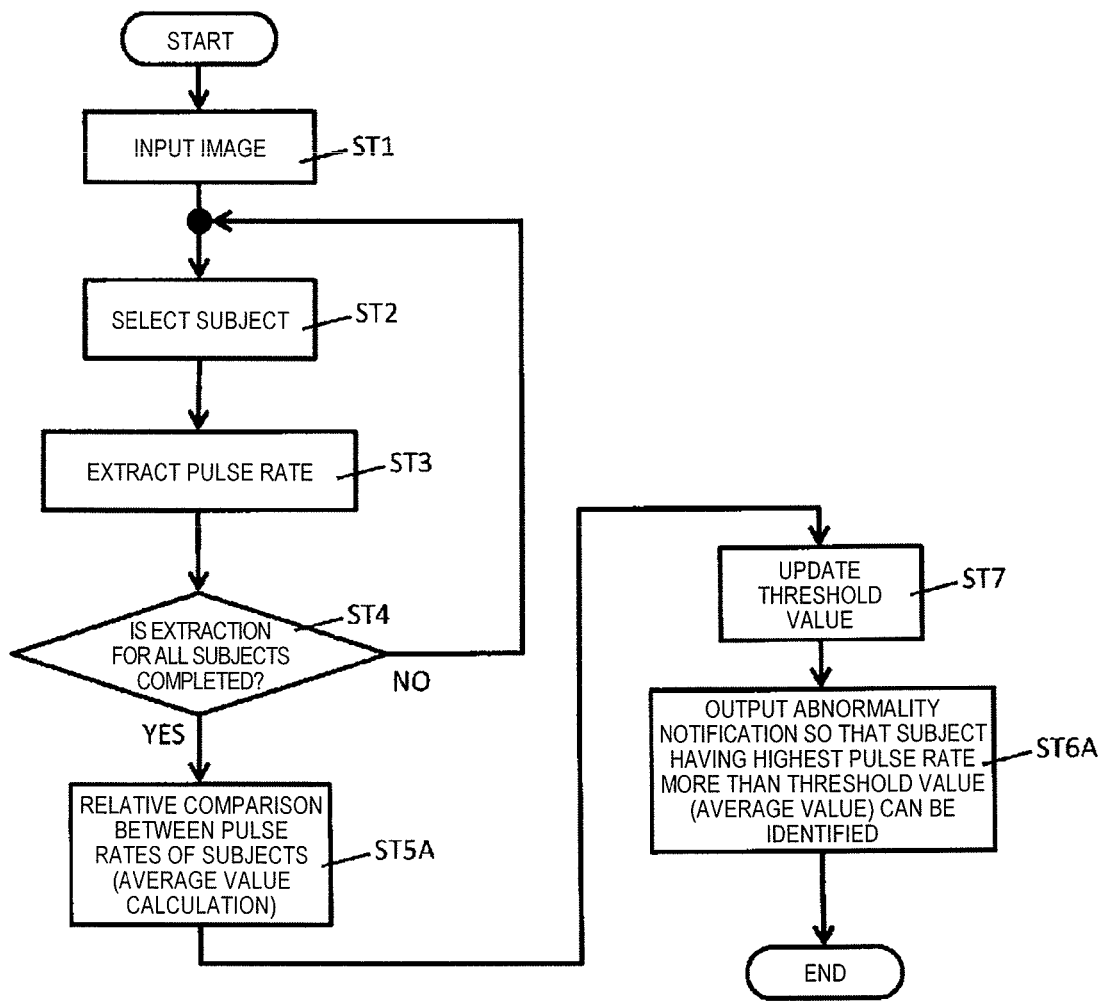
FIG. 9 is a flowchart illustrating examples of operation procedures in the biological information processing device according to the second exemplary embodiment.

Next, with reference to FIG. 9, a description will be made of examples of operation procedures in biological information processing device 10A of the present exemplary embodiment. FIG. 9 is a flowchart illustrating examples of operation procedures in biological information processing device 10A according to the second exemplary embodiment. In description of FIG. 9, the same description as description of FIG. 6 is given the same step number so that the description will be made briefly or will be omitted, and differing content will be described.

In FIG. 9, in a case where subject biological information extraction unit 3 calculates pulse rates of all the subjects (A, B, and C) (ST4, YES), abnormality detection unit 4A calculates an average value of the pulse rate calculation results (estimation results) of the plurality of subjects (A, B, and C) output from subject biological information extraction unit 3 (ST5A), and updates an individual variation of a threshold value stored in threshold value holding/updating unit 5A in advance to the calculated average value (ST7).

Abnormality detection unit 4A performs relative comparison between the respective pulse rates of A, B, and C by using the calculated threshold value (average value) calculated in step ST5A, and excludes A and C as a subject who will possibly be abnormal or a subject as a target requiring special attention since the pulse rate of A and the pulse rate of C are less than the average value (refer to FIG. 8C). Abnormality detection unit 4A detects B whose pulse rate exceeds the average value illustrated in FIG. 8C as a subject who will possibly be abnormal or a subject as a target requiring special attention (ST6A), and outputs the detection result to abnormality notification output unit 6.

Abnormality notification output unit 6 outputs, for example, information regarding at least one subject (for example, B; refer to FIG. 8C) less than n, whose pulse rate exceeds the average value as the threshold value among all of the subjects to monitoring monitor 7 as information regarding a subject who will possibly be abnormal or a subject as a target requiring special attention on the basis of the detection result output from abnormality detection unit 4A (ST6A).

As mentioned above, biological information processing device 10A of the present exemplary embodiment calculates an average value of estimated pulse rates of n subjects (for example, A, B, and C), and detects a subject (for example, B; refer to FIG. 8C) less than n, whose pulse rate exceeds the average value of the pulse rates as a subject who will possibly be abnormal or a subject as a target requiring special attention. Thus, biological information processing device 10A can detects a subject whose pulse rate is more than an average value of pulse rates of all of n estimation target subjects as a subject who will possibly be abnormal or a subject as a target requiring special attention as relative comparison results.

Since biological information processing device 10A can update and hold an average value of estimated pulse rates of n subjects as a threshold value, it is possible to detect a subject having a pulse rate of the subject who will possibly be abnormal or the subject as a target requiring special attention by using a threshold value as the average value updated in the previous estimation and by tracking a change in a surrounding environment, for example, when pulse rates of a plurality of subjects are periodically estimated, compared with a technique using a constant threshold value.

As mentioned above, the biological information processing device according to the first and second exemplary embodiments estimates a pulse rate of a subject as an example of biological information in a noncontact manner by using image data obtained by imaging a target object (for example, a subject, or a processing target; the target object may be not a human but other animals; this is also the same for the following description) without using, for example, a contact type dedicated pulse rate measurement device, and detects and outputs a subject who will possibly be abnormal or a subject as a target requiring special attention on the basis of the estimated pulse rate of the subject.

More specifically, the biological information processing device of each exemplary embodiment receives image data obtained by imaging n (where n is an integer of 2 or more) subjects. Image ranges of the respective subjects are selected from the received image data, and pulse rates of the subjects corresponding to the image ranges are estimated on the basis of image data of the selected image ranges of the respective subjects. The biological information processing device performs relative comparison between the estimated pulse rates of the n subjects so as to detect a subject who will possibly be abnormal or a subject as a target requiring special attention, and outputs information regarding a subject corresponding to the detection result.

The biological information processing device of each exemplary embodiment is, for example, a data terminal such as a desktop or laptop type personal computer (PC), a smart phone, a mobile phone, a tablet terminal, or a personal digital assistant (PDA), and may have a camera function of imaging a person as an example of a target object.

Third Exemplary Embodiment

Figure 10A:
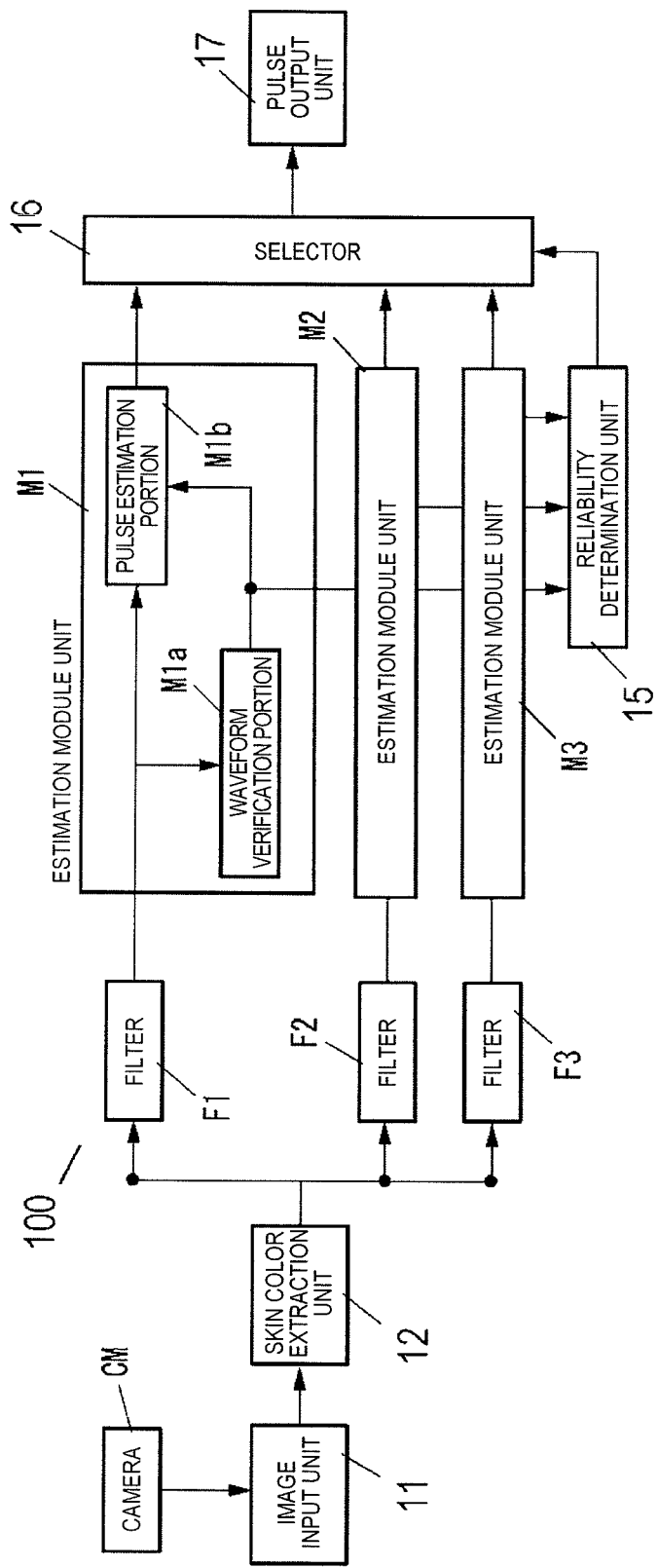
FIG. 10A is a block diagram illustrating an example of an internal configuration of a biological information processing device according to a third exemplary embodiment.
Figure 10B:
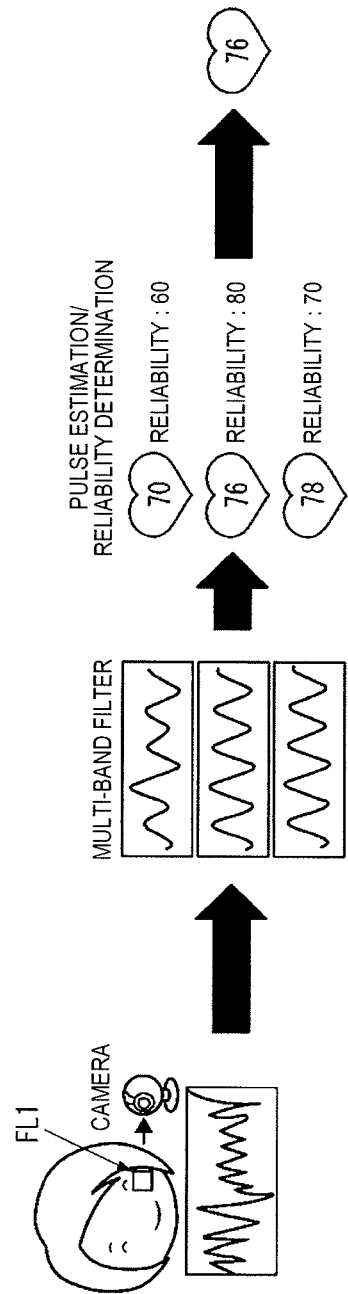
FIG. 10B is a diagram schematically illustrating an example of an operation summary of a biological information processing device according to each exemplary embodiment.

Hereinafter, a description will be made of a configuration of a biological information processing device according to a third exemplary embodiment. FIG. 10A is a block diagram illustrating an example of an internal configuration of biological information processing device 100 according to the third exemplary embodiment. FIG. 10B is a diagram schematically illustrating an operation summary of biological information processing device 100 and 100A (FIG. 16) according to the present exemplary embodiment and a fourth exemplary embodiment which will be described later.

Biological information processing device 100 illustrated in FIG. 10A is configured to include camera CM, image input unit 11, skin color extraction unit 12, a plurality of (for example, three) filters F1, F2 and F3, a plurality of (for example, three) estimation module units M1, M2 and M3, reliability determination unit 15, selector 16, and pulse output unit 17. Estimation module unit M1 is provided to correspond to filter F1, estimation module unit M2 is provided to correspond to filter F2, and estimation module unit M3 is provided to correspond to filter F3.

Camera CM captures an image of a person as a target object at a predetermined frame rate (for example, 10 frames per second (fps)), and outputs the image to image input unit 11. Camera CM may not be included in biological information processing device 100, and may be connected to biological information processing device 100 via, for example, a network. The network is the Internet or an intranet with a wireless network or a wired network as an interface. The wireless network is, for example, a wireless local area network (LAN), a wireless wide area network (WAN), 3G, Long Term Evolution (LTE), or Wireless Gigabit (WiGig). The wired network is, for example, IEEE 802.3 or ETHERNET (registered trademark).

Image input unit 11 continuously receives (acquires), from camera CM, frames of image data obtained by camera CM imaging a person at a predetermined frame rate, and outputs the frames of image data to skin color extraction unit 12. In a case where camera CM is provided separately from biological information processing device 100, image input unit 11 continuously receives frames of image data transmitted from camera CM.

Skin color extraction unit 12 as an example of an extraction unit extracts signals (for example, pixel values or luminance values) indicating a predetermined range (for example, skin color region FL1 illustrated in FIG. 10B) in each frame of the image data which is input from image input unit 11 by using the number of frames corresponding to at least one cycle (the cycle is known). Here, time-series signals extracted by skin color extraction unit 12 are original signals including, for example, noise signals illustrated on the lower part of a person's face illustrated in FIG. 10B. Skin color extraction unit 12 outputs the extracted signals indicating the predetermined range to respective filters F1 to F3.

Filters F1, F2 and F3 are formed of band-pass filters using different filter coefficients, respective operations thereof are the same as each other except that the filter coefficients are different from each other, and thus an operation of filter F1 will be described as an example. Filter F1 averages the signals (pixel values) indicating the predetermined range output from skin color extraction unit 12, for example, so as to remove the noise signals included when camera CM performs imaging.

A pulse wave of the person can be extracted through this averaging, but, since there is a high probability that a motion component of the body or noise may still be included, filter F1 cuts frequency components other than a fundamental frequency of the pulse wave by using a filter coefficient corresponding to filter F1. An output from filter F1 is input to estimation module unit M1.

The filter coefficient of filter F1 is set in advance so that, for example, a signal of 30 to 60 bpm passes through filter F1. The filter coefficient of filter F2 is set in advance so that, for example, a signal of 50 to 90 bpm passes through filter F2. The filter coefficient of filter F3 is set in advance so that, for example, a signal of 70 to 120 bpm passes through filter F3.

Generally, pulses of adults in a stable state show 60 to 80 bpm, but a pass target range is set to 30 to 120 bpm by taking into consideration a case where a subject (a target object or a biological information processing target) has bradycardia or a fast pulse, or the influence during motion or strain. The pass target range of 30 to 120 bpm of the filters is divided into three ranges by respective filters F1 to F3, and thus an output signal from each of filters F1 to F3 is close to a sine wave (refer to each waveform of a multi-band filter illustrated in FIG. 10B). Therefore, it is possible to increase pulse wave estimation accuracy using outputs from respective filters F1 to F3.

Estimation module unit M1 is configured to include waveform verification portion M1a and pulse estimation portion M1b. Hereinafter, configurations of estimation module units M1, M2 and M3 are the same as each other, and thus an operation of estimation module unit M1 will be described as an example.

Figure 14:
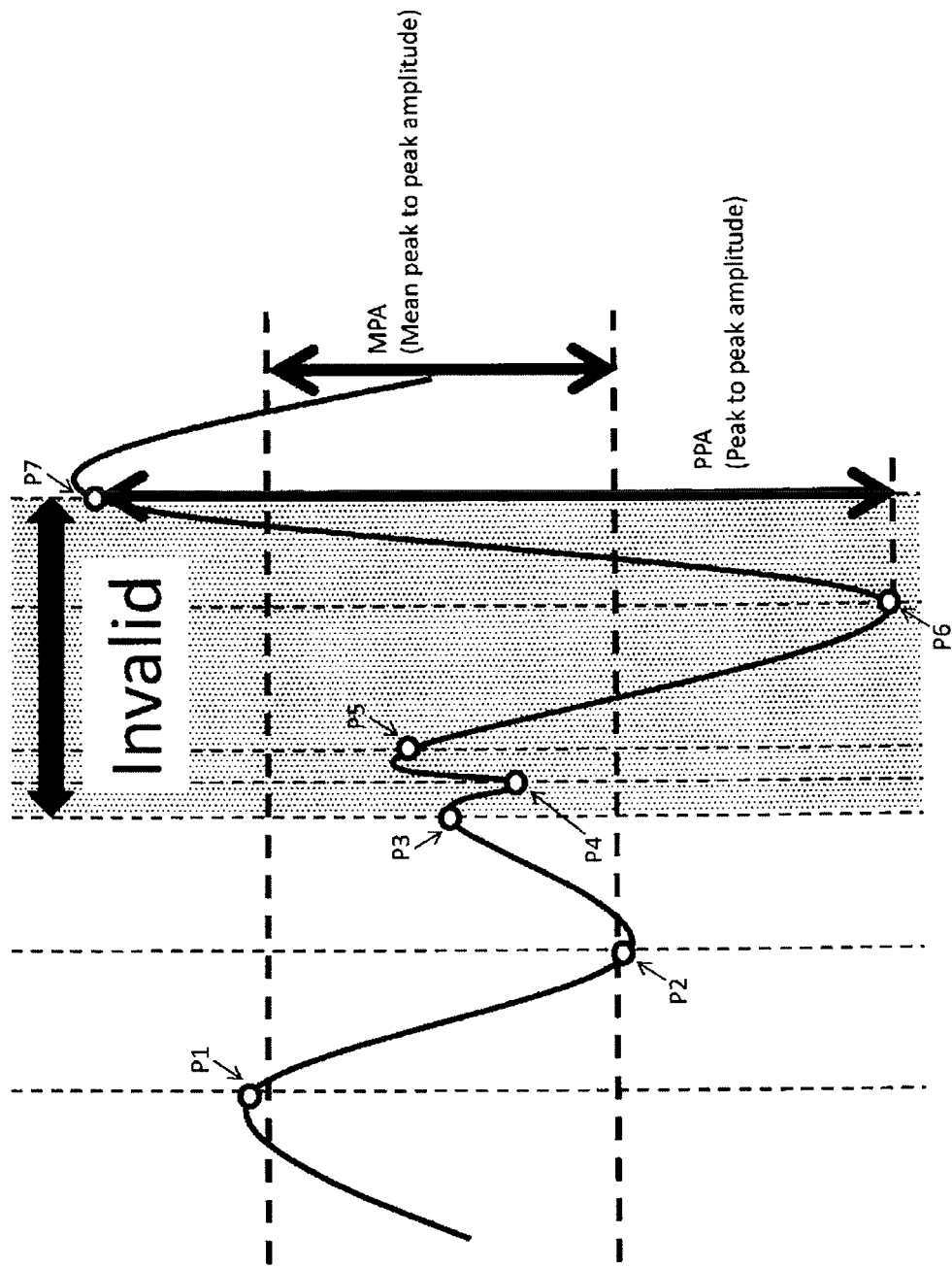
FIG. 14 is a diagram illustrating an operation example of a waveform verification portion of each estimation module unit.

Waveform verification portion M1a as an example of a verification unit receives an output signal of at least one cycle from filter F1, and determines whether or not there is a duration of a signal (that is, a noise signal) satisfying predetermined conditions (that is, Expressions (2) and (3)) in the received output signal of at least one cycle in order to detect a duration of a noise signal which cannot be cut in filter F1. Waveform verification portion M1a excludes a duration of an output signal determined as satisfying the predetermined conditions as an invalid duration (refer to FIG. 14). FIG. 14 is a diagram illustrating an operation example of the waveform verification portion of each of estimation module units M1, M2 and M3.

FIG. 14 illustrates a time-series change in the amplitude of an output signal of at least one cycle from, for example, filter F1, and P1, P2, P3, P4, P5, P6, and P7 are, for example, sampling values having undergone AD conversion in an analog digital converter (ADC) included in waveform verification portion M1a. Mean peak to peak amplitude (MPA) indicates a mean value of the amplitude between peaks corresponding to respective sampling values P1 to P7. Peak to peak amplitude (PPA) indicates the maximum value of the amplitude between the peaks corresponding to respective sampling values P1 to P7.

$$PPA > MPA \times \alpha, \quad 1.0 < \alpha \qquad (2)$$

$$PPA < MPA \times \beta, \quad 1.0 < \beta \qquad (3)$$

Here, $\alpha$ is a coefficient for defining an upper limit which is allowed as the amplitude of an output signal, and $\beta$ is a coefficient for defining a lower limit.

According to Expression (2), waveform verification portion M1a can exclude a signal in which the amplitude of an output signal of at least one cycle from filter F1 is extremely larger than a predetermined value (for example, zero). According to Expression (3), waveform verification portion M1a can exclude a signal in which the amplitude of an output signal of at least one cycle from filter F1 is extremely smaller than a predetermined value (for example, zero). In a case where it is determined that there is a duration of a signal satisfying the predetermined conditions (that is, Expressions (2) and (3)), waveform verification portion M1a outputs a signal of at least one cycle from which the corresponding duration of the signal is excluded, to pulse estimation portion M1b and reliability determination unit 15.

On the other hand, in a case where it is determined that there is no duration of a signal satisfying the predetermined conditions (that is, Expressions (2) and (3)), waveform verification portion M1a outputs the output signal of at least one cycle from filter F1, to pulse estimation portion M1b and reliability determination unit 15 without any change. The process in waveform verification portion M1a uses findings that the amplitude of a person's pulse wave smoothly changes in a predetermined width, and thus there is a high probability that a signal satisfying Expressions (2) and (3) may be disturbance noise. The same output signal is also input to reliability determination unit 15 from the waveform verification portion (not illustrated) of each of other estimation module units M2 and M3.

Figure 13:
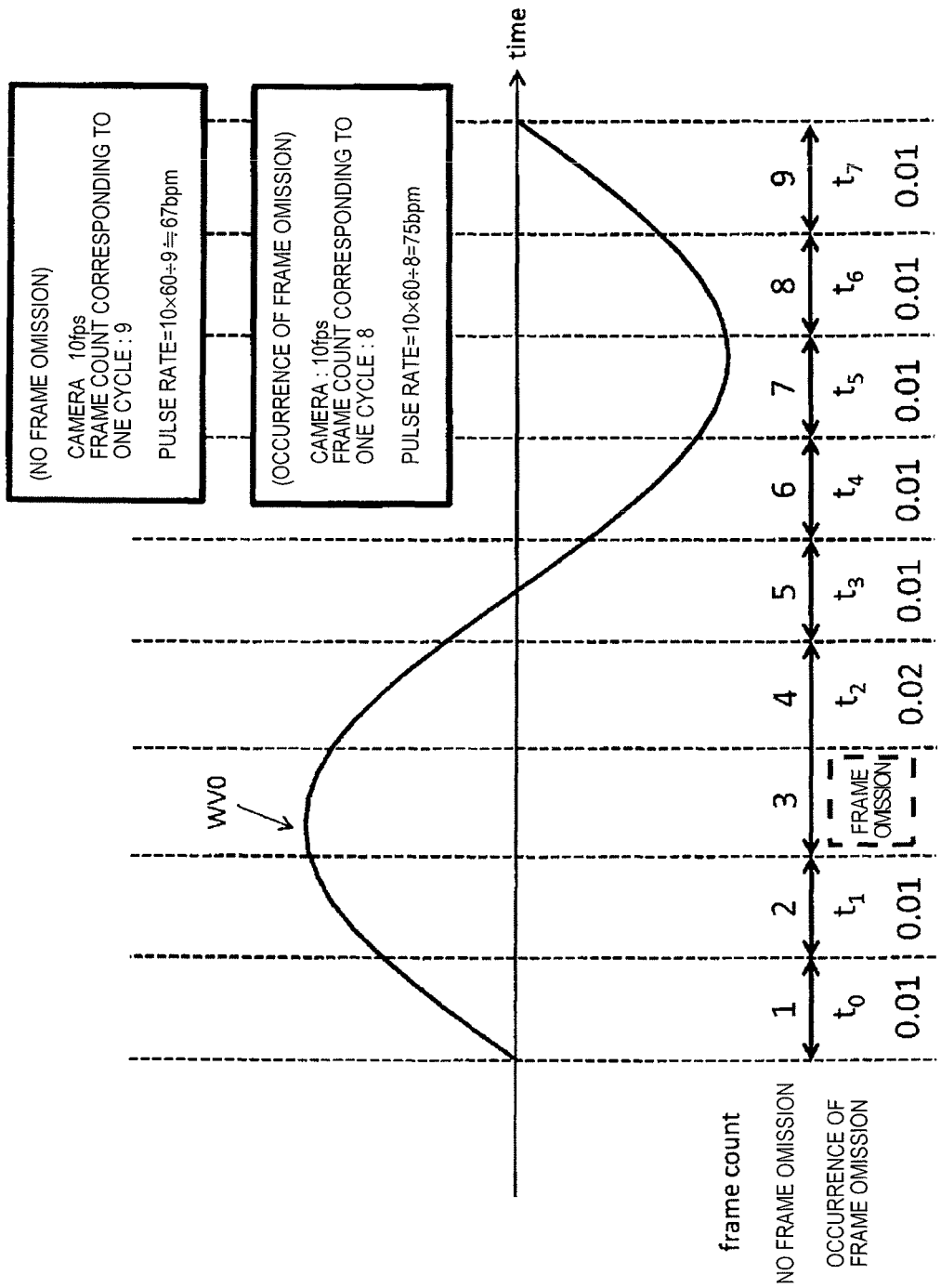
FIG. 13 is a diagram illustrating an example of a pulse calculation method in the biological information processing device according to the third exemplary embodiment.

Pulse estimation portion M1b as an example of an estimation unit calculates a pulse rate of the person according to Equation (4) on the basis of the output signal of at least one cycle from filter F1 or the output signal of at least one cycle from waveform verification portion M1a, and outputs the pulse rate to selector 16 (refer to FIG. 13). FIG. 13 is a diagram illustrating an example of a method of calculating a pulse in biological information processing device 100 according to the second exemplary embodiment.

$$\text{Pulse rate} = 60/PWI \qquad (4)$$

Figure 11:
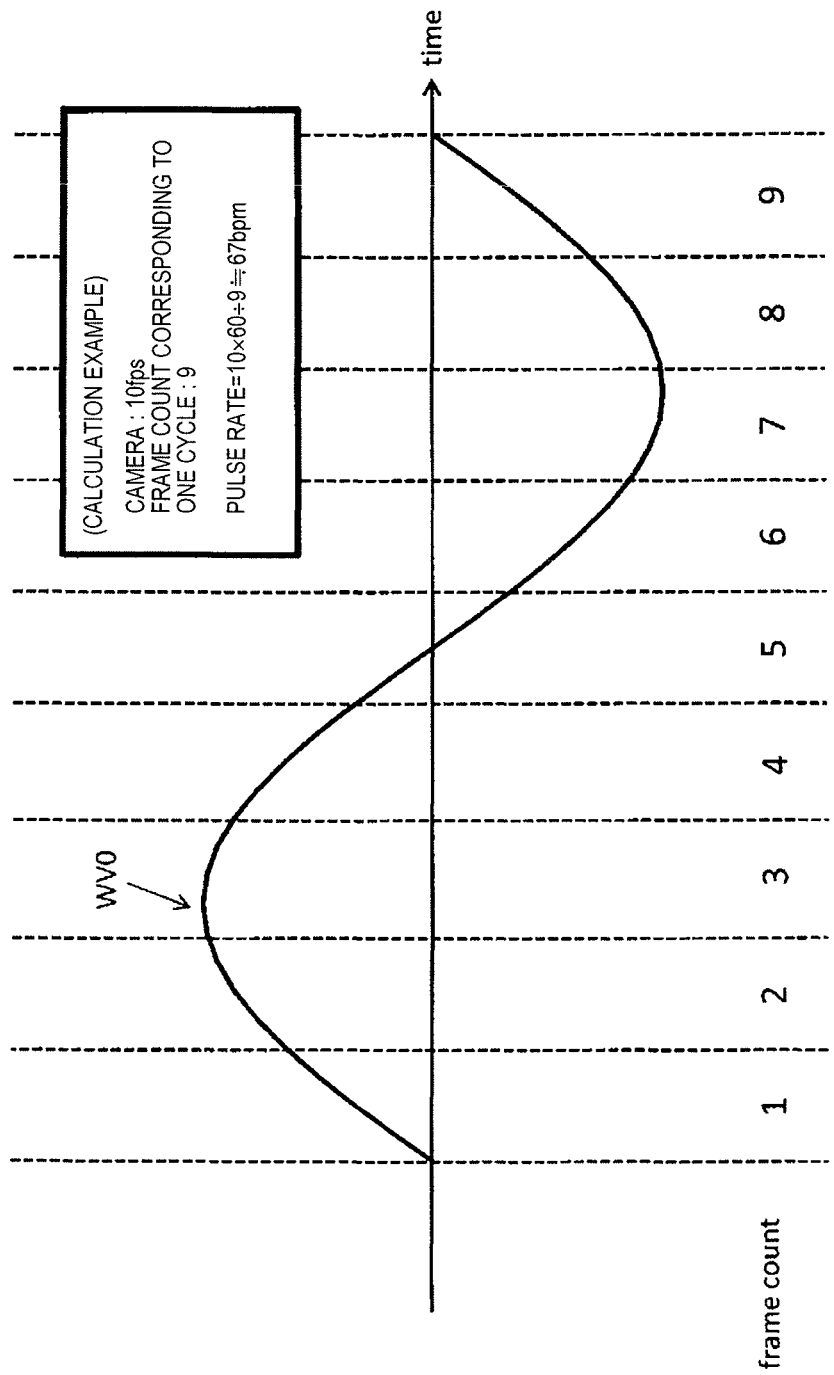
FIG. 11 is a diagram illustrating an example of a pulse calculation method using a camera in the related art.
Figure 12:
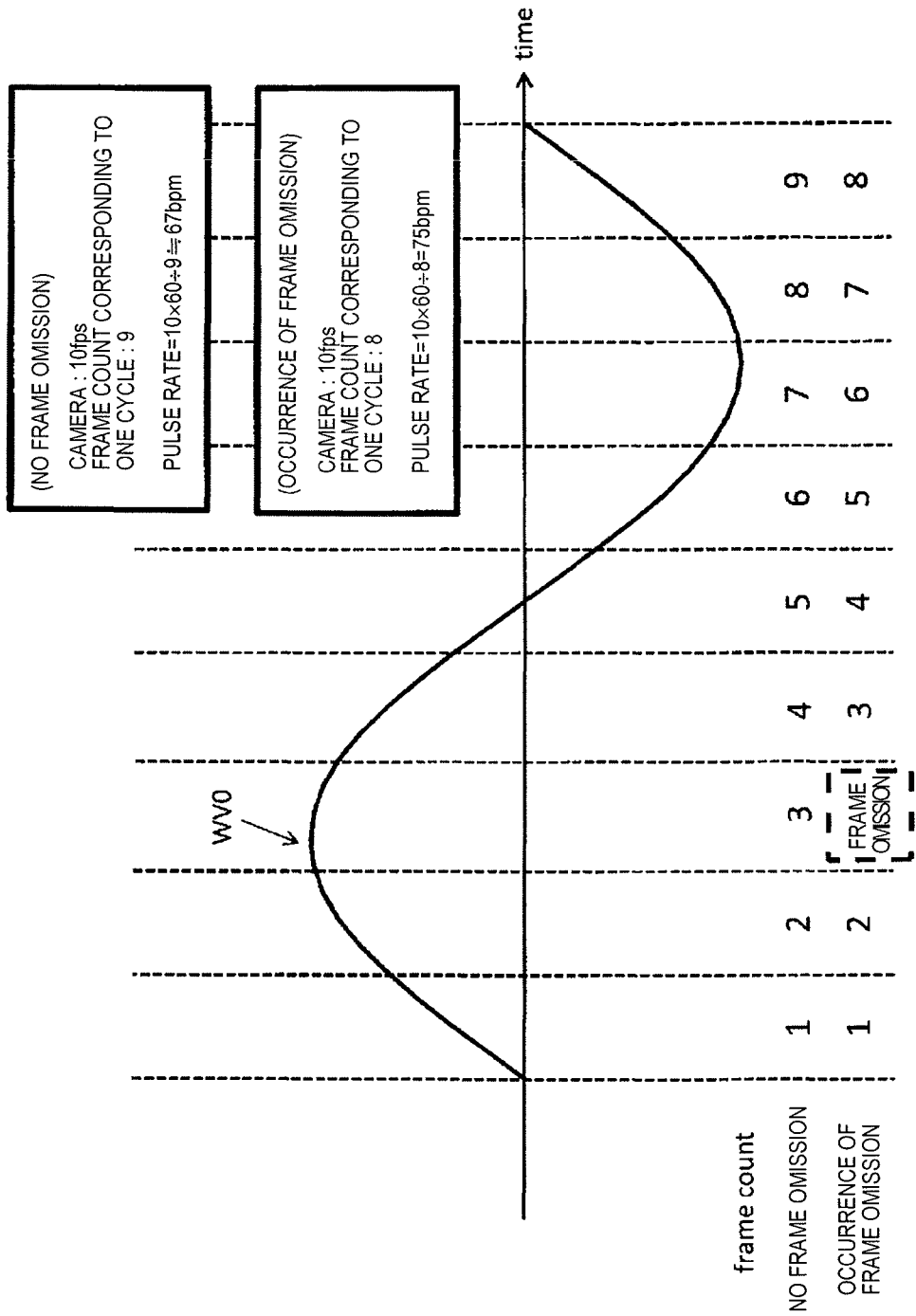
FIG. 12 is a diagram for explaining a problem in the pulse calculation method illustrated in FIG. 11.

Here, with reference to FIGS. 11 and 12, a description will be made of a problem of a pulse calculation method using a camera in the related art. FIG. 11 is a diagram illustrating an example of a pulse calculation method using a camera in the related art. FIG. 12 is a diagram for explaining a problem in the pulse calculation method illustrated in FIG. 11.

In FIG. 11, a transverse axis expresses time, and a longitudinal axis (not illustrated) expresses a green signal WV0 (that is, a pixel value) of one cycle indicating a skin color region in an image captured by a camera, and is expressed in 0 to 255 in a case of being expressed in 8 bits, for example. In FIGS. 11 and 12, for example, by using a calculation result of a difference (that is, a difference from the previous sampling value) between respective sampling values, a signal from a zero point passing time during monotonous increase to a zero point passing time during the next monotonous increase is extracted as signal WV0 of one cycle.

As a pulse rate calculation example illustrated in FIG. 11, in a case where a frame rate of the camera is 10 fps, and a frame count (that is, the number of frames of image data which is required to obtain signal WV0 of one cycle) corresponding to signal WV0 of one cycle is 9, a pulse rate is 10×60/9≅67 bpm.

In FIG. 12, in the same manner as in FIG. 11, a transverse axis expresses time, and a longitudinal axis (not illustrated) expresses green signal WV0 (that is, a pixel value) of one cycle indicating a skin color region in an image captured by a camera, and is expressed in 0 to 255 in a case of being expressed in 8 bits, for example. Here, in a case where omission of a frame (that is, a reception loss on a frame acquisition side or frame missing) of the image data transmitted from the camera occurs, the frame count corresponding to signal WV0 of one cycle is 8, and thus a pulse rate which is different from a pulse rate originally to be calculated is calculated so that an error occurs. In other words, if frame omission occurs, a pulse rate is 10×60/8=75 bpm, and thus a difference (8 bpm) from 67 bpm occurs as an error.

Therefore, biological information processing devices 100 and 100A of the respective exemplary embodiments including the present exemplary embodiment calculates a pulse rate in pulse estimation portion M1b according to Equation (4) by using a sum of input intervals (for example, input interval or reception intervals from camera CM) of frames of image data which is input from image input unit 11 until signal WV0 of one cycle is obtained, without using a frame count corresponding to signal WV0 of one cycle.

In FIG. 13, in the same manner as in FIG. 11, a transverse axis expresses time, and a longitudinal axis (not illustrated) expresses a signal extracted by skin color extraction unit 12. In other words, the signal illustrated in FIG. 13 indicates green signal WV0 (that is, a pixel value) of one cycle indicating a skin color region in an image captured by camera CM, and is expressed in 0 to 255 in a case of being expressed in 8 bits, for example. Pulse estimation portion M1b uses a sum (=0.01+0.01+0.02+0.01+0.01+0.01+0.01+0.01) of input intervals t0, t1, t2, t3, t4, t5, t6 and t7 of frames of image data required to obtain signal WV0 of one cycle, as PWI (pulse wave interval) shown in the above Equation (4).

Therefore, in FIG. 13, in a case where a third frame is omitted, the number of frames of image data required to obtain signal WV0 of one cycle is 8. However, pulse estimation portion M1b uses a sum of the input intervals t0, t1, t2, t3, t4, t5, t6 and t7 of frames of image data required to obtain signal WV0 of one cycle, including the input interval t2 until the second frame is input and then the next frame (the fourth frame illustrated in FIG. 13) is input. Consequently, pulse estimation portion M1b can calculate an appropriate pulse rate in the same manner as in a case where frame omission does not occur in FIG. 11 (refer to Equation (4)).

Reliability determination unit 15 as an example of a determination unit determines an output signal of at least one cycle from an estimation module unit, having the smallest number of invalid durations, on the basis of output signals of at least one cycle from respective estimation module units M1, M2 and M3 from which durations of output signals from filters F1, F2 and F3 satisfying the predetermined conditions (Expression (3) and Equation (4)) are excluded, or output signals from filters F1, F2 and F3 not satisfying the predetermined conditions. In other words, the output signals from filters F1, F2 and F3 are signals output from respective estimation module units M1, M2 and M3 without any change. Reliability determination unit 15 outputs a determination result (that is, information regarding any one of the estimation module units) to selector 16.

Reliability determination unit 15 applies reliability of "100" as reliability, for example, in a case where there no invalid duration, and applies reliability by using a predetermined calculation method (a method of multiplying the number of invalid durations by a predetermined weighting factor (known) for each of Expressions (2) and (3) based on determination of the invalid durations and subtracting a point from "100") according to the number of invalid durations satisfying Expression (2), the number of invalid durations satisfying Expression (3), or the number of invalid durations satisfying both of Expressions (2) and (3).

Selector 16 as an example of an output unit selects an output (information regarding the pulse rate) from the estimation module unit corresponding to the determination result in reliability determination unit 15 from among the outputs (that is, information regarding pulse rates estimated in respective estimation module units M1, M2 and M3) from estimation module units M1, M2 and M3 on the basis of the determination result output from reliability determination unit 15, and outputs the selected output to pulse output unit 17.

For example, as illustrated in FIG. 10B, it is assumed that a pulse rate estimated in estimation module unit M1 is "70", the reliability determined in reliability determination unit 15 is "60", a pulse rate estimated in estimation module unit M2 is "76", the reliability determined in reliability determination unit 15 is "80", a pulse rate estimated in estimation module unit M3 is "78", and the reliability determined in reliability determination unit 15 is "70". In this case, selector 16 outputs the pulse rate of "76" causing the highest reliability of "80" to be obtained, to pulse output unit 17.

Pulse output unit 17 as an example of an output unit outputs information regarding the pulse rate selected by selector 16. For example, in a case where biological information processing device 100 includes a display (not illustrated), pulse output unit 17 displays the information regarding the pulse rate selected by selector 16 on the display. For example, in a case where biological information processing device 100 includes a speaker (not illustrated), pulse output unit 17 outputs the information regarding the pulse rate selected by selector 16 from the speaker.

Figure 15:
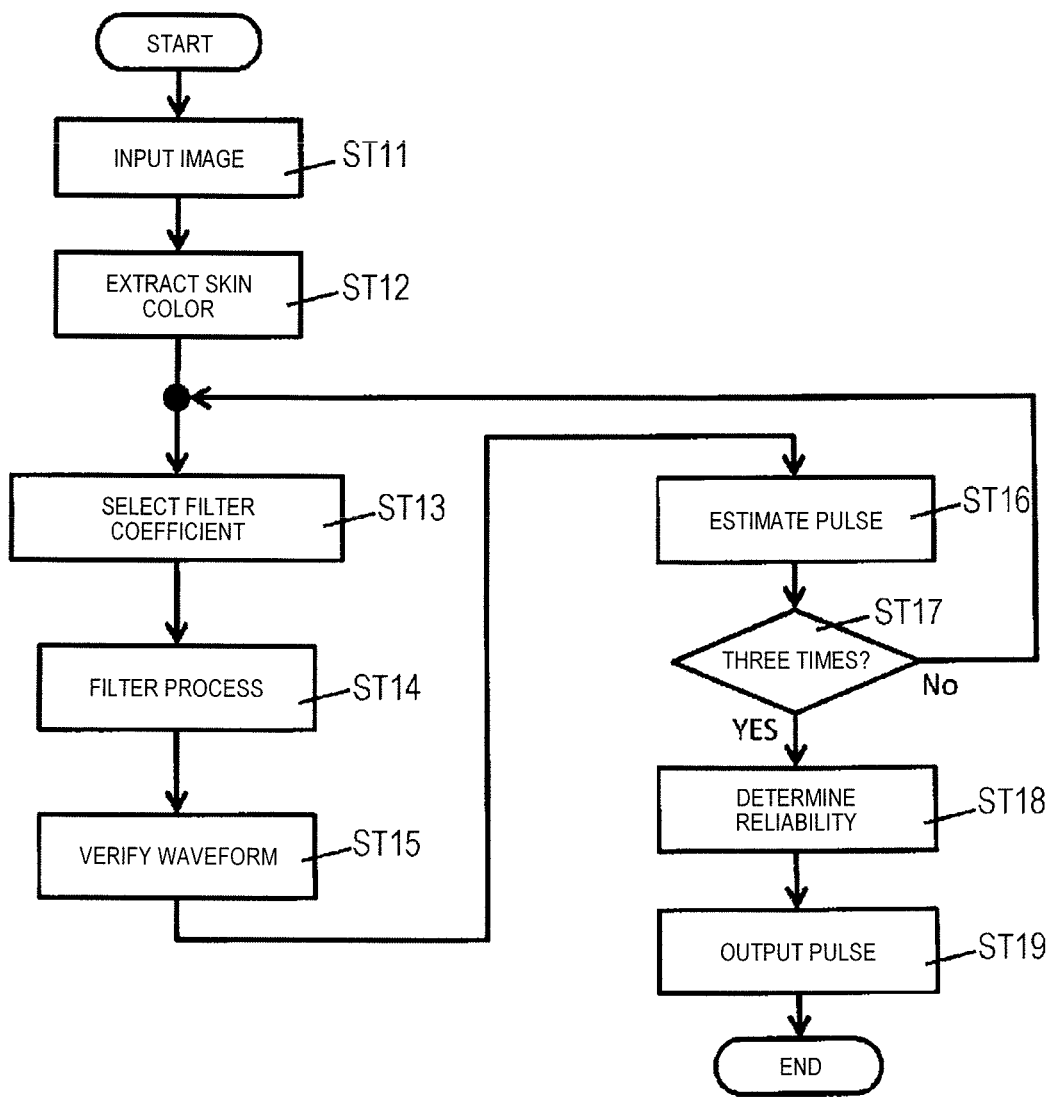
FIG. 15 is a flowchart illustrating examples of operation procedures in the biological information processing device according to the third exemplary embodiment.

Next, with reference to FIG. 15, a description will be made of examples of operation procedures in biological information processing device 100 of the present exemplary embodiment. FIG. 15 is a flowchart illustrating examples of operation procedures in biological information processing device 100 according to the second exemplary embodiment.

In FIG. 15, image input unit 11 continuously receives (acquires), from camera CM, frames of image data obtained by camera CM imaging a person at a predetermined frame rate, and outputs the frames of image data to skin color extraction unit 12 (ST11). Skin color extraction unit 12 extracts signals (for example, pixel values or luminance values) indicating a predetermined range (for example, skin color region FL1 illustrated in FIG. 10B) in each frame of the image data which is input from image input unit 11 by using the number of frames corresponding to at least one cycle (the cycle is known) (ST12). Skin color extraction unit 12 outputs the extracted signals indicating the predetermined range to respective filters F1 to F3.

In step ST13, filter coefficients for filters F1 to F3 are selected (ST13). As described above, the filter coefficient of filter F1 is set in advance so that, for example, a signal of 30 to 60 bpm passes through filter F1. The filter coefficient of filter F2 is set in advance so that, for example, a signal of 50 to 90 bpm passes through filter F2. The filter coefficient of filter F3 is set in advance so that, for example, a signal of 70 to 120 bpm passes through filter F3. In FIG. 15, for better understanding of description, the processes in step ST13 to step ST17 are shown in a time series, but the respective processes are performed in parallel in biological information processing device 100.

As an example of a filter process, filter F1 averages the signals (pixel values) indicating the predetermined range output from skin color extraction unit 12, for example, so as to remove noise signals included when camera CM performs imaging (ST14). As another example of the filter process, filter F1 cuts frequency components other than a fundamental frequency of the pulse wave by using the filter coefficient corresponding to filter F1 (ST14). An output from filter F1 is input to estimation module unit M1.

Waveform verification portion M1a determines whether or not there is a duration of a signal satisfying predetermined conditions (that is, Expressions (2) and (3)) in a received output signal of at least one cycle in order to detect a duration of a noise signal which cannot be cut in filter F1 on the basis of the output signal of at least one cycle from filter F1, and thus verifies a waveform (ST15).

Waveform verification portion M1a excludes a duration of an output signal determined as satisfying the predetermined conditions as an invalid duration, and outputs a signal of at least one cycle from which the corresponding duration of the signal is excluded, to pulse estimation portion M1b and reliability determination unit 15. On the other hand, in a case where it is determined that there is no duration of a signal satisfying the predetermined conditions (that is, Expressions (2) and (3)), waveform verification portion M1a outputs the output signal of at least one cycle from filter F1, to pulse estimation portion M1b and reliability determination unit 15 without any change.

Pulse estimation portion M1b calculates a pulse rate of the person according to Equation (4) on the basis of the output signal of at least one cycle from filter F1 or the output signal of at least one cycle from waveform verification portion M1a, and outputs the pulse rate to selector 16 (ST16).

In step ST17, in a case where a process in each of filters F1 to F3 and estimation module units M1 to M3 is not finished (ST17, NO), an operation of biological information processing device 100 is in a waiting state until the processes in step ST13 to step ST17 are completed in each of filters F1 to F3 and estimation module units M1 to M3.

On the other hand, in a case where a process in each of filters F1 to F3 and estimation module units M1 to M3 is finished (ST17, YES), reliability determination unit 15 performs the next process in step ST18. An output signal of at least one cycle from an estimation module unit, having the smallest number of invalid durations, is determined on the basis of output signals of at least one cycle from respective estimation module units M1, M2 and M3 from which durations of output signals from filters F1, F2 and F3 satisfying the predetermined conditions are excluded, or output signals from filters F1, F2 and F3 not satisfying the predetermined conditions. The predetermined conditions are, for example, Expression (3) and Equation (4). Reliability determination unit 15 outputs a determination result (that is, information regarding any one of the estimation module units) to selector 16.

Selector 16 selects an output (information regarding the pulse rate) from the estimation module unit corresponding to the determination result in reliability determination unit 15 from among the outputs (that is, information regarding pulse rates estimated in respective estimation module units M1, M2 and M3) from estimation module units M1, M2 and M3 on the basis of the determination result output from reliability determination unit 15, and outputs the selected output to pulse output unit 17 (ST19). Pulse output unit 17 outputs information regarding a pulse rate selected by selector 16 (ST19).

As mentioned above, biological information processing device 100 of the present exemplary embodiment extracts signals indicating a predetermined range (for example, skin color region FL1 of a person) of input image data, and outputs signal corresponding to different coefficients (for example, filter coefficients) among the extracted signals indicating the predetermined range from a plurality of filters F1 to F3. Biological information processing device 100 estimates a pulse rate of the person on the basis of an output signal of at least one cycle from a corresponding filter and input intervals of frames of image data corresponding to the output signal of at least one cycle in estimation module units M1 to M3 provided to respectively correspond to filters F1 to F3. Any one of a plurality of estimated pulse rates is selected according to output signals from the plurality of filters F1 to F3, and is output.

Consequently, even in a case where frames of image data obtained by imaging a user are omitted, biological information processing device 100 estimates a pulse rate of the user by using input intervals of a plurality of frames of the image data corresponding to a signal of at least one cycle obtained through an image process (for example, a noise removal process using a predetermined filter coefficient) on a skin color region of the user included in the image data, and the property that blood absorbs light in a specific wavelength range. Thus, biological information processing device 100 can estimate a pulse rate of a user in a noncontact manner with high accuracy without using, for example, a contact type dedicated pulse rate measurement device.

In biological information processing device 100, the estimation module unit corresponding to each filter excludes a duration of an output signal from a filter, satisfying a predetermined condition, as an invalid duration, and estimates a pulse rate of a person on the basis of an output signal of at least one cycle from which the invalid duration is excluded and input intervals of frames of image data corresponding to the output signal of at least one cycle.

Consequently, biological information processing device 100 can exclude a duration (for example, a duration of a signal whose amplitude is extremely larger than a predetermined value or amplitude is extremely smaller than the predetermined value) of an output signal from a filter, satisfying a predetermined condition, as an invalid duration. Thus, for example, it is possible to reduce the influence of disturbance noise, and also to estimate a pulse rate of a person with high accuracy by using input intervals of frames of image data corresponding to an output signal of at least one cycle from which an invalid duration is excluded.

Biological information processing device 100 determines an output signal of at least one cycle, having the smallest number of invalid durations on the basis of an output signal of at least one cycle from which a duration of an output signal from each filter, satisfying a predetermined condition, is excluded, and selects a pulse rate of a person, estimated so as to correspond to the determined output signal of at least one cycle.

Consequently, biological information processing device 100 can select a pulse rate of a person, using an output signal of at least one cycle having the smallest number of invalid durations (in other words, with the least influence of disturbance noise).

Fourth Exemplary Embodiment

Figure 16:
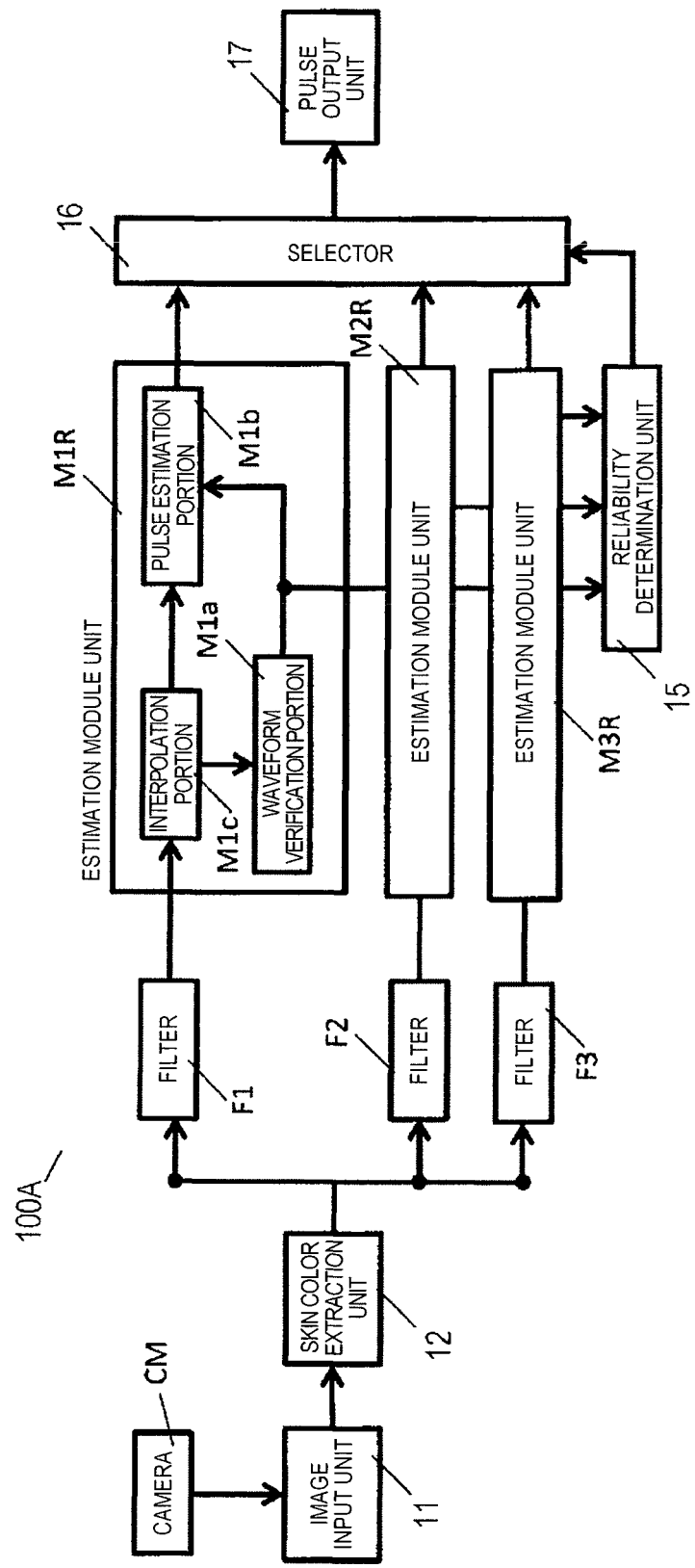
FIG. 16 is a block diagram illustrating an example of an internal configuration of a biological information processing device according to a fourth exemplary embodiment.
Figure 17:
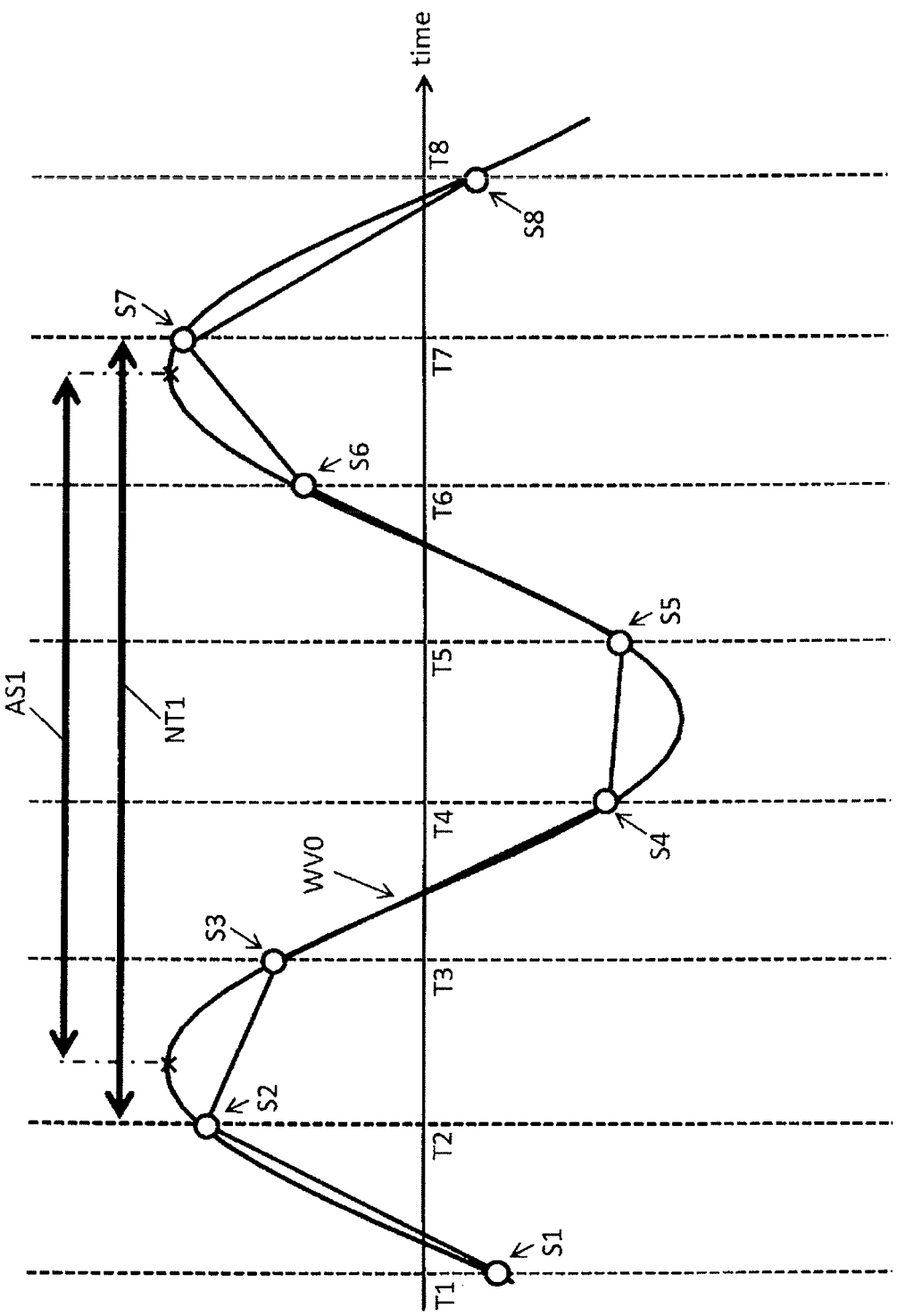
FIG. 17 is a diagram for explaining a problem in a case where a peak of an observed waveform corresponding to one cycle is deviated relative to a sampling position.

FIG. 16 is a block diagram illustrating an example of an internal configuration of biological information processing device 100A according to the fourth exemplary embodiment. FIG. 17 is a diagram for explaining a problem in a case where a peak of an observed waveform corresponding to one cycle is deviated relative to a sampling position. In biological information processing device 100A illustrated in FIG. 16, units having the same configurations as the respective units of biological information processing device 100 illustrated in FIG. 10A are given the same reference numerals so that description thereof will be made briefly or omitted, and differing content will be described.

Biological information processing device 100A illustrated in FIG. 16 is configured to include camera CM, image input unit 11, skin color extraction unit 12, a plurality of (for example, three) filters F1, F2 and F3, a plurality of (for example, three) estimation module units M1R, M2R and M3R, reliability determination unit 15, selector 16, and pulse output unit 17. Estimation module unit M1R is provided to correspond to filter F1, estimation module unit M2R is provided to correspond to filter F2, and estimation module unit M3R is provided to correspond to filter F3.

Estimation module unit M1R is configured to include interpolation portion M1c, waveform verification portion M1a, and pulse estimation portion M1b. Interpolation portion M1c receives an output signal of at least one cycle from filter F1, interpolates (for example, linearly interpolates) a difference (time difference) between positions (time points) at which the output signal of at least one cycle from filter F1 becomes a predetermined value (for example, zero) on the basis of the output signal of at least one cycle from filter F1, and outputs the interpolated output signal of at least one cycle to waveform verification portion M1a and pulse estimation portion M1b. In the present embodiment, waveform verification portion M1a and the pulse estimation portion M1b use the output from interpolation portion M1c. Hereinafter, configurations of estimation module units M1R, M2R and M3R are the same as each other, and thus an operation of estimation module unit M1R will be described as an example.

Here, with reference to FIG. 17, a description will be made of a problem in a case where a peak of an observed waveform of one cycle is deviated relative to a sampling position. In FIG. 17, a transverse axis expresses time, and a longitudinal axis (not illustrated) expresses signal WV0 extracted by skin color extraction unit 12. In other words, the signal illustrated in FIG. 17 indicates green signal WV0 (that is, a pixel value) of one cycle indicating skin color region FL1 in an image captured by camera CM, and is expressed in 0 to 255 in a case of being expressed in 8 bits, for example.

In FIG. 17, S1 to S8 indicate, for example, sampling values having AD conversion in the ADC included in waveform verification portion M1a, and T1 to T8 indicate sampling time points at which the ADC performs AD conversion. One cycle of signal WV0 illustrated in FIG. 17 is accurately a time period (refer to line segment AS1) between a peak of signal WV0 and the next peak, but, the peak of signal WV0 is deviated relative to a sampling position (a sampling value at a sampling time point), an error occurs. Specifically, one cycle of signal WV0 illustrated in FIG. 17 is a time period (refer to line segment NT1) between sampling time point T2 of sampling value S2 which is a peak value and sampling time point T7 of sampling value S7 which is the next peak value, and thus an error corresponding to a difference between line segment AS1 and line segment NT1 occurs. Therefore, errors occur in signals which are input to filters F1 to F3, and thus estimation accuracy of a pulse of a person deteriorates.

Figure 18:
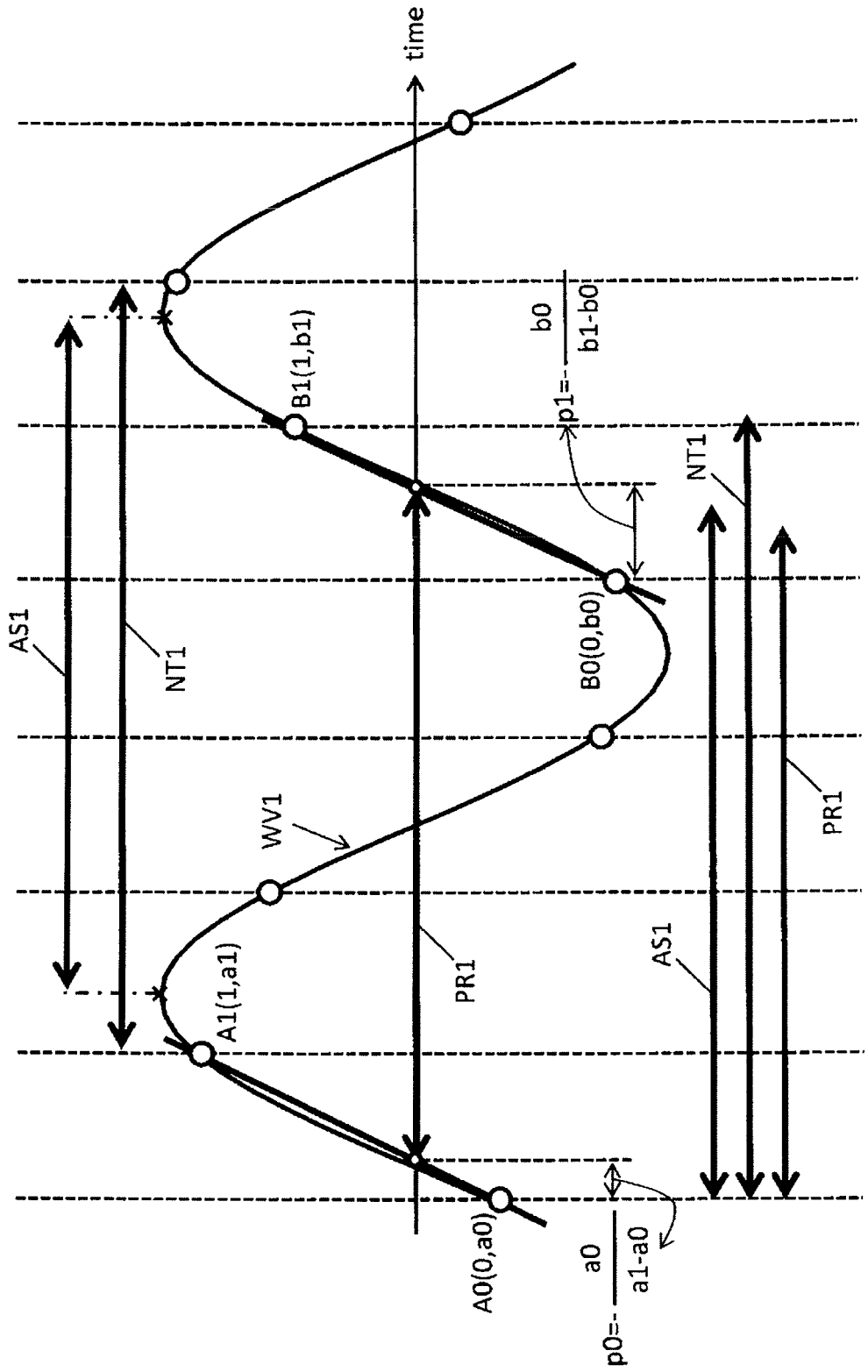
FIG. 18 is a diagram illustrating a first example of an operation of an interpolation portion of each estimation module unit.
Figure 19:
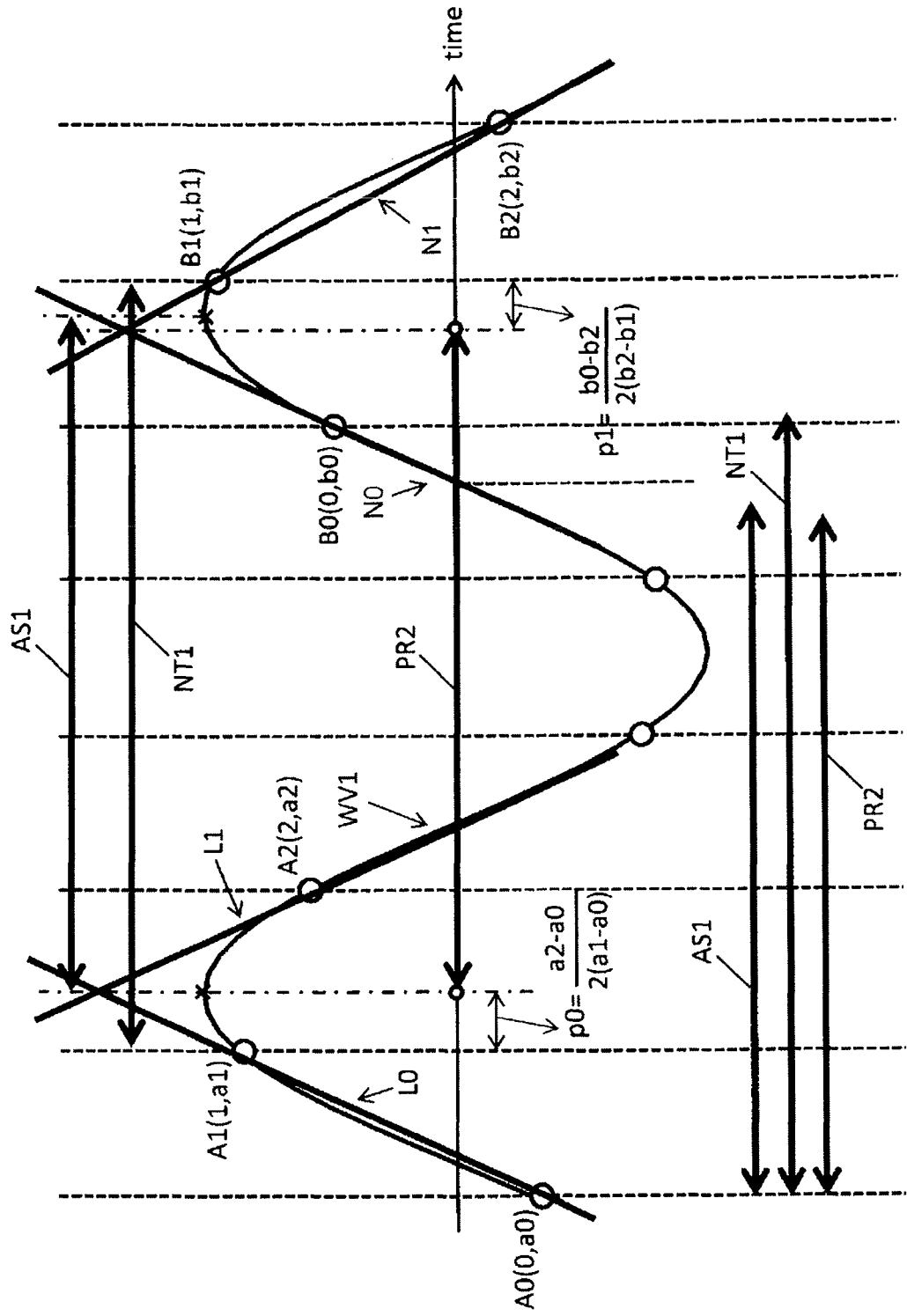
FIG. 19 is a diagram illustrating a second example of an operation of the interpolation portion of each estimation module unit.
Figure 20:
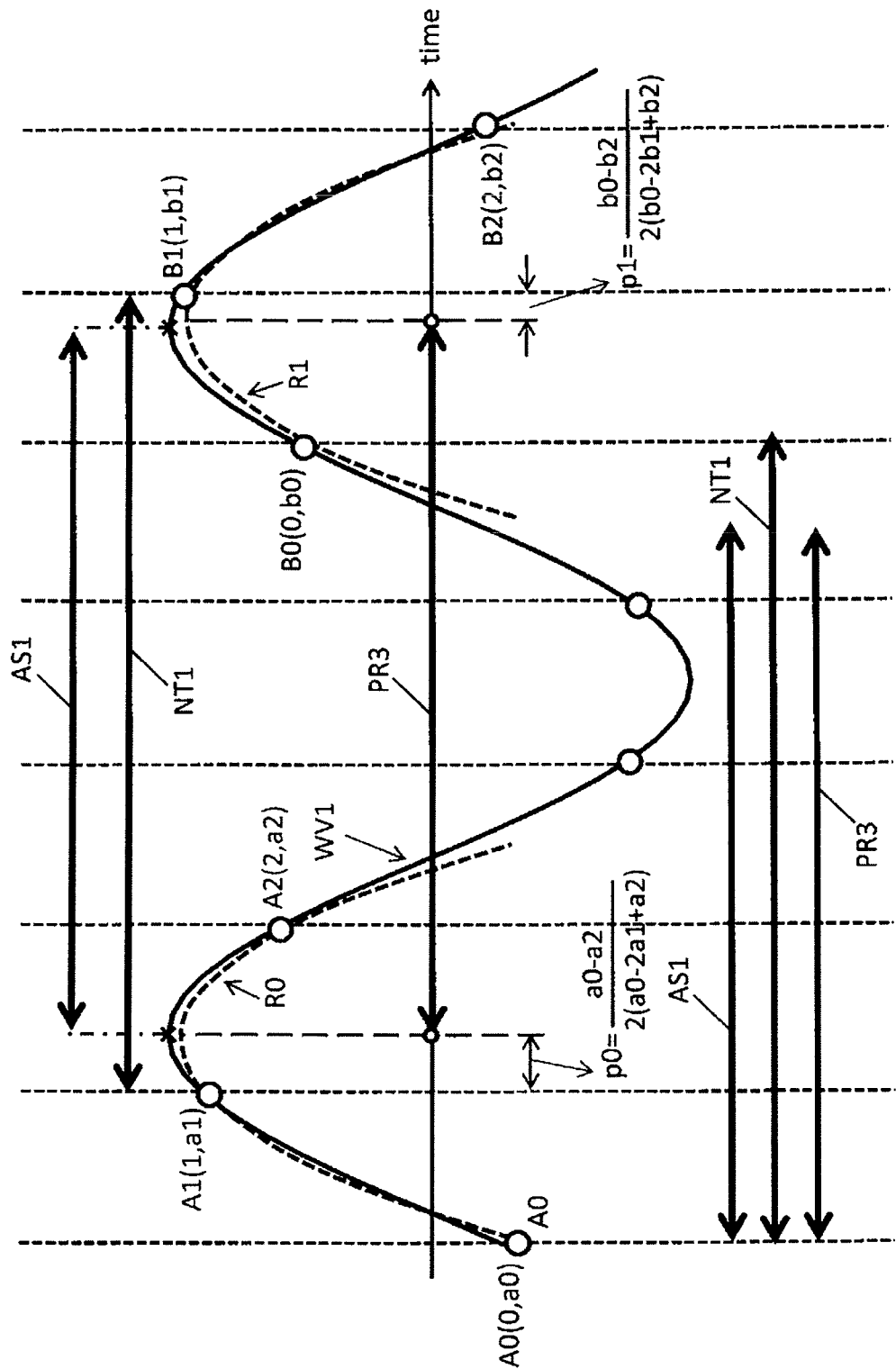
FIG. 20 is a diagram illustrating a third example of an operation of the interpolation portion of each estimation module unit.

Therefore, in the present exemplary embodiment, each of estimation module units M1R to M3R derives signal WV0 of one cycle by interpolating a signal (that is, an output signal from each of filters F1 to F3) which is input to each of estimation module units M1R to M3R in order to accurately obtain the PWI (pulse wave interval) shown in the above Equation (4) (refer to FIGS. 18, 19 and 20).

First Interpolation Example

FIG. 18 is a diagram illustrating a first example of an operation of interpolation portion M1c of each estimation module unit. In FIG. 18, a transverse axis expresses time, and a longitudinal axis (not illustrated) expresses signal WV1 extracted by skin color extraction unit 12. In other words, the signal illustrated in FIG. 18 indicates green signal WV1 (that is, a pixel value) of one cycle indicating skin color region FL1 in an image captured by camera CM, and is expressed in 0 to 255 in a case of being expressed in 8 bits, for example.

In the first interpolation illustrated in FIG. 18, interpolation portion M1c interpolates (that is, a linear interpolation process), for example, a difference (time difference) between at least two positions (time points) on the transverse axis at which signal WV1 during monotonous increase or monotonous decrease passes through a predetermined value (for example, zero), so as to estimate signal WV1 of at least one cycle. Line segment AS1 and line segment NT1 illustrated in FIG. 18 are the same as line segment AS1 and line segment NT1 illustrated in FIG. 17, and thus a description thereof will be omitted, and this is also the same for FIGS. 19 and 20. On lower parts in FIGS. 18 to 20, lengths of line segments AS1 and NT1 are compared with a length of line segment PR1, PR2 or PR3.

More specifically, interpolation portion M1c estimates, for example, a difference (refer to line segment PR1) between a position at which signal WV1 during monotonous increase passes through zero and a position at which signal WV1 during the next monotonous increase passes through zero. For this, the interpolation portion obtains a position (a left end of line segment PR1) at which a line segment passing through at least two positions (point A0 (0,a0) and point A1 (1,a1)) of signal WV1 during first monotonous increase passes through zero, and a position (a right end of line segment PR1) at which a line segment passing through at least two positions (point B0 (0,b0) and point B1 (1,b1)) of signal WV1 during second monotonous increase passes through zero. Here, a0, a1, b0, and b1 are sampling values at respective positions on signal WV1. In FIG. 18, the description is made by using the points on signal WV1 during monotonous increase, but the same applies for a case of using points on signal WV1 during monotonous decrease.

Distance p0 between the position of the point A0 on the transverse axis and the left end of line segment PR1 is expressed by Equation (5) according to linear interpolation in interpolation portion M1c. Similarly, distance p1 between the position of the point B0 on the transverse axis and the right end of line segment PR1 is expressed by Equation (6) according to linear interpolation in interpolation portion M1c. Consequently, interpolation portion M1c can calculate a length of line segment PR1, and thus an error with line segment AS1 can be reduced compared with line segment NT1 in which an error with line segment AS1 is large. Therefore, it is possible to improve pulse rate estimation accuracy.

$$p0 = -\frac{a0}{a1 - a0} \quad (5)$$

$$p1 = -\frac{b0}{b1 - b0} \quad (6)$$

Second Interpolation Example

FIG. 19 is a diagram illustrating a second example of an operation of interpolation portion M1c of each estimation module unit. In FIG. 19, a transverse axis expresses time, and a longitudinal axis (not illustrated) expresses signal WV1 extracted by skin color extraction unit 12. In other words, the signal illustrated in FIG. 19 indicates green signal WV1 (that is, a pixel value) of one cycle indicating skin color region FL1 in an image captured by camera CM, and is expressed in 0 to 255 in a case of being expressed in 8 bits, for example.

In the second interpolation example illustrated in FIG. 19, interpolation portion M1c obtains, for example, an intersection between a straight line passing through two points on signal WV1 during monotonous increase or monotonous decrease in which an initial peak is obtained, and a straight line having an inclination obtained by inverting an inclination of the straight line and passing through a single point on signal WV1 during monotonous increase or monotonous decrease. Similarly, interpolation portion M1c obtains, for example, an intersection between a straight line passing through two points on signal WV1 during monotonous increase or monotonous decrease in which the next peak is obtained, and a straight line having an inclination obtained by inverting an inclination of the straight line and passing through a single point on signal WV1 during monotonous increase or monotonous decrease. Interpolation portion M1c performs interpolation (that is, equiangular straight line fitting) by using the two intersections so as to estimate signal WV1 of at least one cycle.

More specifically, interpolation portion M1c obtains, for example, an intersection between straight line L0 passing through two points (point A0 (0,a0) and point A1 (1,a1)) on signal WV1 during monotonous increase and straight line L1 having an inclination obtained by inverting an inclination of the straight line L0 and passing through a single point (point A2 (2,a2)) on signal WV1 during monotonous decrease. Similarly, interpolation portion M1c obtains, for example, an intersection between straight line N1 passing through two points (point B1 (1,b1) and point B2 (2,b2)) on signal WV1 during monotonous decrease and straight line N0 having an inclination obtained by inverting an inclination of the straight line N1 and passing through a single point (point B0 (0,b0)) on signal WV1 during monotonous increase. Here, a0, a1, a2, b0, b1, and b2 are sampling values at respective positions on signal WV1. In FIG. 19, the description is made by using the points on signal WV1 during monotonous increase for straight lines L0 and N0 and the points on signal WV1 during monotonous decrease for straight lines L1 and N1, but the same applies for a case where monotonous decrease is replaced with monotonous decrease.

Line segment PR2 indicates a difference between a position of the intersection on the transverse axis between straight line L0 and straight line L1 and a position of the intersection on the transverse axis between straight line N0 and straight line N1. Distance p0 between the position of point A1 on the transverse axis and the position on the transverse axis between straight line L0 and straight line L1 is expressed by Equation (7) according to equiangular straight line fitting in interpolation portion M1c. Similarly, distance p1 between the position on the transverse axis between straight line N0 and straight line N1 and the position of point B1 on the transverse axis is expressed by Equation (8) according to equiangular straight line fitting in interpolation portion M1c. Consequently, interpolation portion M1c can calculate a length of line segment PR2, and thus an error with line segment AS1 can be reduced compared with line segment NT1 in which an error with line segment AS1 is large. Therefore, it is possible to improve pulse rate estimation accuracy.

$$p0 = \frac{a2 - a0}{2(a1 - a0)} \quad (7)$$

$$p1 = \frac{b0 - b2}{2(b2 - b1)} \quad (8)$$

Third Interpolation Example

FIG. 20 is a diagram illustrating a third example of an operation of interpolation portion M1c of each estimation module unit. In FIG. 20, a transverse axis expresses time, and a longitudinal axis (not illustrated) expresses signal WV1 extracted by skin color extraction unit 12. In other words, the signal illustrated in FIG. 20 indicates green signal WV1 (that is, a pixel value) of one cycle indicating skin color region FL1 in an image captured by camera CM, and is expressed in 0 to 255 in a case of being expressed in 8 bits, for example.

In the third interpolation example illustrated in FIG. 20, interpolation portion M1c performs interpolation (that is, parabola fitting) by using an apex of a quadratic curve passing through three points on signal WV1 in which an initial peak is obtained and an apex of a quadratic curve passing through three points on signal WV1 in which the next peak is obtained, and thus estimates signal WV1 of at least one cycle.

More specifically, interpolation portion M1c obtains, for example, a position on the transverse axis of an apex of quadratic curve R0 passing through three points (point A0 (0,a0), point A1 (1,a1), and point A2 (2,a2)) on signal WV1 in which the initial peak is obtained, and a position on the transverse axis of an apex of quadratic curve R1 passing through three points (point B0 (0,b0), point B1 (1,b1), and point B2 (2,b2)) on signal WV1 in which the next peak is obtained. Here, a0, a1, a2, b0, b1, and b2 are sampling values at respective positions on signal WV1.

Line segment PR3 indicates a difference between the position of the apex of quadratic curve R0 on the transverse axis and the position of the apex of quadratic curve R1 on the transverse axis. Distance p0 between the position of point A1 on the transverse axis and the position of the apex of quadratic curve R0 on the transverse axis is expressed by Equation (9) according to parabola fitting in interpolation portion M1c. Similarly, distance p1 between the position of point B1 on the transverse axis and the position of the apex of quadratic curve R1 on the transverse axis is expressed by Equation (10) according to parabola fitting in interpolation portion M1c. Consequently, interpolation portion M1c can calculate a length of line segment PR3, and thus an error with line segment AS1 can be reduced compared with line segment NT1 in which an error with line segment AS1 is large. Therefore, it is possible to improve pulse rate estimation accuracy.

$$p0 = \frac{a0 - a2}{2(a0 - 2a1 + a2)} \quad (9)$$

$$p1 = \frac{b0 - b2}{2(b2 - 2b1 + b2)} \quad (10)$$

Figure 21:
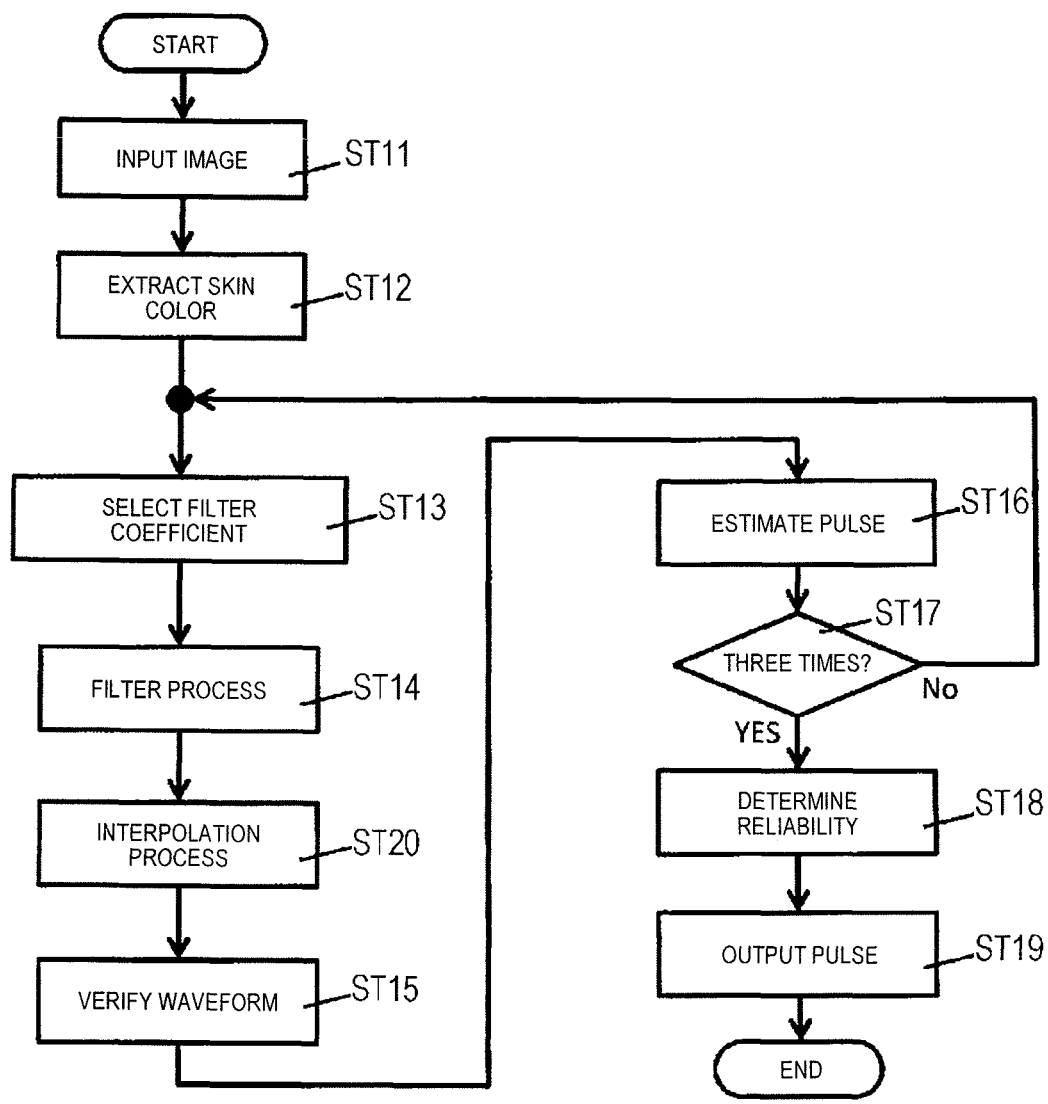
FIG. 21 is a flowchart illustrating examples of operation procedures in the biological information processing device according to the fourth exemplary embodiment.

FIG. 21 is a flowchart illustrating examples of operation procedures in biological information processing device 100A according to the fourth exemplary embodiment. In FIG. 21, the content which is different from that of the operation procedures in biological information processing device 100 of the third exemplary embodiment will be described, and the same operation is given the same step number so that a description thereof will be made briefly or will be omitted.

In FIG. 21, after step ST14, interpolation portion M1c receives an output signal of at least one cycle from filter F1, interpolates (for example, linearly interpolates) a difference (time difference) between positions (time points) at which the output signal of at least one cycle from filter F1 becomes a predetermined value (for example, zero) on the basis of the output signal of at least one cycle from filter F1, and outputs the interpolated output signal of at least one cycle to waveform verification portion M1a and pulse estimation portion M1b (ST20). Waveform verification portion M1a and the pulse estimation portion M1b use the output from interpolation portion M1c.

For example, waveform verification portion M1a receives an output signal of at least one cycle from interpolation portion M1c, and determines whether or not there is a duration of a signal (that is, a noise signal) satisfying predetermined conditions (that is, Expressions (2) and (3)) in the received output signal of at least one cycle in order to detect a duration of a noise signal which cannot be cut in filter F1 (ST15). Pulse estimation portion M1b calculates a pulse rate of the person according to Equation (4) on the basis of the output signal of at least one cycle from interpolation portion M1c or the output signal of at least one cycle from waveform verification portion M1a, and outputs the pulse rate to selector 16 (ST16). Details of the process in step ST15 or step ST16 are the same as those in the second exemplary embodiment, and thus a description thereof will be omitted. Processes in step ST16 and the subsequent steps are the same as those in FIG. 15, and thus a description thereof will be omitted.

As mentioned above, biological information processing device 100A of the present exemplary embodiment interpolates a difference between time points at which output signals of at least one cycle from filters F1, F2 and F3 become a predetermined value (for example, zero) on the basis of the output signals of at least one cycle from respective filters F1, F2 and F3 corresponding to estimation module units M1R, M2R and M3R, and outputs interpolated output signals of at least one cycle from the filters.

Consequently, biological information processing device 100A can obtain the output signals of at least one cycle from filters F1, F2 and F3 with high accuracy. Thus, even in a case where a peak of an output signal of one cycle is deviated relative to a sampling position, it is possible to minimize an error between an accurate time difference between peaks of an output signal to be originally obtained and an actually obtained time difference between peaks of an output signal from the filter. Therefore, it is possible to estimate a more accurate pulse rate of a person.

As mentioned above, the biological information processing device according to the third and fourth exemplary embodiments includes an image input unit that inputs image data obtained by imaging a person, an extraction unit, a plurality of filter, a plurality of estimation units, and an output unit. The extraction unit extracts signals indicating a predetermined range of image data which is input from the image input unit. The plurality of filters respectively output signals corresponding to different coefficients among the signals indicating the predetermined range extracted by the extraction unit by using the different coefficients. The plurality of estimation units are respectively provided to correspond to the plurality of filters, and estimate pulse rates of the person on the basis of outputs of one cycle from corresponding filters and input intervals of frames of image data corresponding to the outputs. The output unit selects any one of a plurality of pulse rates estimated by the plurality of estimation units according to the outputs from the plurality of filters, and outputs the selected pulse rate.

A biological information processing method according to the present disclosure includes the following steps: a step of inputting image data obtained by imaging a person; a step of extracting signals indicating a predetermined range of the input image data; a step of outputting respective signals corresponding to different coefficients among the extracted signals indicating the predetermined range by using a plurality of filters having the different coefficients; a step of estimating pulse rates of the person on the basis of outputs of one cycle from corresponding filters and input intervals of frames of image data corresponding to the outputs; and a step of selecting any one of a plurality of estimated pulse rates according to the outputs from the plurality of filters, and outputting the selected pulse rate.

According to the present disclosure, even in a case where frames of image data obtained by imaging a user are omitted, it is possible to estimate a pulse rate of the user with high accuracy in a noncontact manner by performing an image process on a skin color region of the user included in acquired image data.

The biological information processing device according to each exemplary embodiment estimates a pulse rate of a person as an example of biological information in a noncontact manner by using image data obtained by imaging a target object (a processing target; for example, a person; the target object may be other animals; this is also the same for the following description) without using, for example, a contact type dedicated pulse rate measurement device.

More specifically, the biological information processing device of each exemplary embodiment receives frames of image data obtained by imaging a person, extracts a signal (pixel value) indicating a predetermined range (for example, a skin color region) of the received image data, and outputs respective signals corresponding to different coefficients among the extracted signals indicating the predetermined range from the filters. In the biological information processing device, the estimation module units respectively corresponding to the filters estimate pulse rates of a person on the basis of output signals of at least one cycle from the filters and input intervals of frames of image data corresponding to the output signals, and any one of a plurality of pulse rates estimated by the plurality of estimation module units is selected and output according to the output signals from the filters.

The biological information processing device of each exemplary embodiment is, for example, a data terminal such as a desktop or laptop type personal computer (PC), a smart phone, a mobile phone, a tablet terminal, or a personal digital assistant (PDA), and may have a camera function for imaging a person as an example of a target object.

As mentioned above, various exemplary embodiments have been described with reference to the drawings, but, needless to say, the present disclosure is not limited to such exemplary embodiments. It is clear that a person skilled in the art can conceive of various modifications or alterations within the scope disclosed in the claims, and it is understood that they are also naturally included in the technical scope of the present disclosure.

INDUSTRIAL APPLICABILITY

The present invention is useful as a biological information processing device and a biological information processing method capable of detecting accurately and in real time a pulse rate of a subject who will possibly be abnormal or a subject as a target requiring special attention among a plurality of subjects by tracking a change in a surrounding environment even in a case where the change in the surrounding environment occurs.

REFERENCE MARKS IN THE DRAWINGS 1 image input unit
2 subject region selection unit
3 subject biological information extraction unit
4, 4A abnormality detection unit
5, 5A threshold value holding/updating unit
6 abnormality notification output unit
7 monitoring monitor
10, 10A, 100, 100A biological information processing device
11 image input unit
12 skin color extraction unit
15 reliability determination unit
16 selector
17 pulse output unit
AP1, APk abnormality notification acquisition device
CM camera
F1, F2, F3 filter
FL1 skin color region
M1, M2, M3, M1R, M2R, M3R estimation module unit
M1a waveform verification portion
M1b pulse estimation portion
M1c interpolation portion

The invention claimed is:

1. A biological information processing device comprising:
a memory that stores instructions; and
a processor which, when executing the instructions stored in the memory, performs operations comprising:
  inputting image data capturing a plurality of processing targets;
  extracting biological information data including pulse rates, from the plurality of the processing targets respectively captured in the input image data;
  calculating a threshold based on the extracted biological information data from the plurality of processing targets;
  detecting a target of the plurality of processing targets which is abnormal or requires special attention according to relative comparison between the calculated threshold the extracted biological information data from the plurality of the processing targets;
  outputting information with respect to the detected target;
  storing a predetermined threshold used for a determination to specify the detected target which is abnormal or requires special attention; and
  updating the predetermined threshold with the calculated threshold.

2. The biological information processing device of claim 1, wherein
the detected target corresponds to a processing target of which the extracted biological information data is the highest in the plurality of processing targets.

3. The biological information processing device of claim 2, wherein the processor, when executing the instructions stored in the memory, further performs operations comprising:
  updating the predetermined threshold with the highest biological information data from among plurality of processing targets.

4. The biological information processing device of claim 1, wherein
the detected target corresponds to a processing target of which the extracted biological information data is higher than the calculated threshold.

5. The biological information processing device of claim 1, wherein the processor, when executing the instructions stored in the memory, further performs operations comprising:
  updating the predetermined threshold according to the relative comparison between the extracted biological information data from the plurality of the processing targets.

6. A biological information processing method comprising:
  inputting image data capturing a plurality of processing targets;
  extracting biological information data including pulse rates, from the plurality of the processing targets respectively captured in the input image data;
  calculating a threshold based on the extracted biological information data from the plurality of processing targets;
  detecting a target of the plurality of processing targets which is abnormal or requires special attention according to relative comparison between the calculated threshold and the extracted biological information data from the plurality of the processing targets;
  outputting information with respect to the detected target;
  storing a predetermined threshold used for a determination to specify the detected target which is abnormal or requires special attention; and
  updating the predetermined threshold with the calculated threshold.

7. The biological information processing method of claim 6, wherein
the detected target corresponds to a processing target of which the extracted biological information data is the highest in the plurality of processing targets.

8. The biological information processing method of claim 7, further comprising:
  updating the predetermined threshold with the highest biological information data from among plurality of processing targets.

9. The biological information processing method of claim 6, wherein
the detected target corresponds to a processing target of which the extracted biological information data is higher than the calculated threshold.

10. The biological information processing method of claim 6, further comprising:
  updating the predetermined threshold according to the relative comparison between the extracted biological information data from the plurality of the processing targets.

11. A biological information processing method comprising:
  inputting image data capturing a plurality of processing targets;
  extracting biological information data including pulse rates from the plurality of the processing targets respectively captured in the input image data;
  detecting a target of the plurality of processing targets which is abnormal or requires special attention according to a variable threshold calculated based on the extracted biological information data from the plurality of the processing targets;
  outputting information with respect to the detected target;
  storing a predetermined threshold used for a determination to specify the detected target which is abnormal or requires special attention; and
  updating the predetermined threshold with the calculated variable threshold.

12. The biological information processing method of claim 11, wherein
the detected target corresponds to a processing target of which the extracted biological information data is the highest in the plurality of processing targets.

13. The biological information processing method of claim 12, further comprising:
  updating the threshold with the highest biological information data from among plurality of processing targets.

14. The biological information processing method of claim 11, wherein
the detected target corresponds to a processing target of which the extracted biological information data is higher than the calculated threshold.

15. The biological information processing method of claim 11, further comprising:
  updating the predetermined threshold according to the relative comparison between the extracted biological information data from the plurality of the processing targets.

* * * * *